US008092992B2

(12) United States Patent
Kuwabara et al.

(10) Patent No.: US 8,092,992 B2
(45) Date of Patent: Jan. 10, 2012

(54) TRANSCRIPTIONAL REGULATION OF GENE EXPRESSION BY SMALL DOUBLE-STRANDED MODULATORY RNA

(75) Inventors: Tomoko Kuwabara, Ibaraki (JP); Fred H. Gage, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 10/857,784

(22) Filed: May 28, 2004

(65) Prior Publication Data

US 2005/0226848 A1    Oct. 13, 2005

Related U.S. Application Data

(60) Provisional application No. 60/474,422, filed on May 29, 2003, provisional application No. 60/553,791, filed on Mar. 16, 2004.

(51) Int. Cl.
| | |
|---|---|
| C12Q 1/68 | (2006.01) |
| C12N 5/00 | (2006.01) |
| C12N 5/02 | (2006.01) |
| A61K 48/00 | (2006.01) |
| C07H 21/04 | (2006.01) |
| C07H 21/02 | (2006.01) |

(52) U.S. Cl. ........... 435/6; 435/325; 435/375; 514/44 R; 536/23.1
(58) Field of Classification Search ............ 514/44; 435/6, 69.1, 4, 375; 536/23.4
See application file for complete search history.

(56) References Cited

U.S. PATENT DOCUMENTS

| | | | | |
|---|---|---|---|---|
| 5,935,811 A | * | 8/1999 | Anderson et al. | ............ 435/69.1 |
| 6,479,653 B1 | * | 11/2002 | Natesan et al. | ............... 536/23.4 |
| 6,506,559 B1 | | 1/2003 | Fire et al. | |
| 2003/0143732 A1 | | 7/2003 | Fosnaugh et al. | |

FOREIGN PATENT DOCUMENTS
WO    WO 2005/001110    1/2005

OTHER PUBLICATIONS

Jedrusik et al., A single histon H1 isoform (H1.1) is esential for chromatin silencing and germline development in Caenorhabditis elegans., 2001, Development, vol. 128, pp. 1069-1080.*
Opalinska et al., Nucleic-acid therapeutics: basic principles and recent applications, Jul. 2002, Nature Reviews, vol. 1, pp. 503-514.*
Tuschl et al., Small Interfering RNAs: A revolutionary tool for the anaylsis of gene function and gene therapy., Molecular Interventions, Jun. 2002, vol. 2, pp. 158-167.*
Abbas-Terki et al., Lentiviral-Mediated RNA Interference, Dec. 10, 2002, Human Gene Therapy, vol. 13, pp. 2197-2201.*
Bosher et al., RNA interference can target pre-mRNA: Consequences for gene expression in a Caenorhabditis elegans Operon, Nov. 1999, Genetics, vol. 153, pp. 1245-1256.*
Seth et al., Repressor element silencing transcription factor/neuron-restrictive silencing factor (REST/NRSF) can act as an enhancer as well as a repressor of corticotropin-releasing hormone gene transcription, 2001, The Journal of Biological Chemistry, vol. 276, pp. 13917-13923.*
Sullenger et al., Analysis of trans-acting response decoy RNA-mediated inhibition of human immunodeficiency virus type I transactivation, 1991, Journal of Virology, vol. 65, pp. 6811-6816.*
Gewirtz et al., Nucleic Acid Therapeutics: State of the art and future prospects, 1998, Blood, vol. 92, pp. 712-736.*
Morishita et al., Application of transcription factor "decoy" strategy as means of gene therapy and study of gene expression in cardiovascular disease, 1998, Circulation Research, vol. 82, pp. 1023-1028.*
Novina et al., The RNAi revolution, 2004, Nature, vol. 430, pp. 161-164.*
Clusel et al., Ex vivo regulation of specific gene expression by nanomolar concentration of double-stranded dumbbell oligonucleotides, 1993, Nucleic Acids Research, vol. 21, pp. 3405-3411.*
International Search Report and Written Opinion from PCT Application No. US04/17208.
Andrés et al., "CoREST: A functional corepressor required for regulation of neural-specific gene expression," *Proc. Natl. Acad. Sci. USA*, 96:9873-9878 (1999).
Brené et al., "Regulation of GluR2 promoter activity by neurotrophic factors via a neuron-restrictive silencer element," *European Journal of Neuroscience*, 12:1525-1533 (2000).
Chen et al., "NRSF/REST is required in vivo for repression of multiple neuronal target genes during embryogenesis," *Nature Genetics*, 20:136-142 (1998).
Grimes et al., "The Co-repressor mSin3A is a Functional Component of the REST-CoRest Repressor Complex," *The Journal of Biological Chemistry*, 275(13):9461-9467 (2000).
Huang et al., "Transcriptional repression by REST: recruitment of Sin3A and histone deacetylase to neuronal genes," *Nature Neuroscience*, 2(10):867-872 (1999).
Kallunki et al., "The neural restrictive silencer element can act as both a repressor and enhancer of L1 cell adhesion molecule gene expression during postnatal development," *Proc. Natl. Acad. Sci. USA*, 95:3233-3238 (1998).
Kempermann et al., "Early determination and long-term persistence of adult-generated new neurons in the hippocampus of mice," *Development*, 130:391-399 (2003).

(Continued)

*Primary Examiner* — Dana Shin
(74) *Attorney, Agent, or Firm* — Klarquist Sparkman, LLP

(57) ABSTRACT

The invention provides a method for modulating gene expression by contacting a cellular system with a double-stranded ribonucleic acid molecule capable of associating with a regulatory machinery that controls transcription of one or more genes, wherein the association results in altered expression of the one or more genes. The invention is further directed to method for directing the differentiation of neuronal stem cells into neurons by contacting a cellular system with a double-stranded ribonucleic acid molecule capable of associating with a regulatory machinery that controls transcription of one or more genes involved in neuronal differentiation and directing the transcription of the one or more genes. In related embodiments, the invention provides particular compositions of double-stranded ribonucleic acid molecules as well as therapeutic and screening applications of the invention.

13 Claims, 11 Drawing Sheets

OTHER PUBLICATIONS

Kim, "No Effect of Expression of Neuron-Restrictive Silencer Factor (NRSF) Protein on N-Type $Ca^{2+}$ Channel $\alpha_{1B}$ Gene Promoter Activity in NS20Y Cells," *Molecules and Cells*, 8(5):600-605 (1998).

Kraner et al., "Silencing the Type II Sodium Channel Gene: A Model for Neural-Specific Gene Regulation," *Neuron*, 9:37-44 (1992).

Lunyak et al., "Corepressor-Dependent Silencing of Chromosomal Regions Encoding Neuronal Genes," *Science*, 298:1747-1752 (2002).

Miyoshi et al., "Development of a Self-Inactivating Lentivirus Vector," *Journal of Virology*, 72(10):8150-8157 (1998).

Mori et al., "Effect of age on the gene expression of neural-restrictive silencing factor NRSF/REST," *Neurobiology of Aging*, 23:255-262 (2002).

Myers et al., "Transcriptional Regulation of the GluR2 Gene: Neural-Specific Expression, Multiple Promoters, and Regulatory Elements," *The Journal of Neuroscience*, 18(17):6723-6739 (1998).

Naldini et al., "In Vivo Gene Delivery and Stable Transduction of Nondividing Cells by a Lentiviral Vector," *Science*, 272:263-267 (1996).

Naruse et al., "Neural restrictive silencer factor recruits mSin3 and histone deacetylase complex to repress neuron-specific target genes," *Proc. Natl. Acad. Sci. USA*, 96(24):13691-13696 (1999).

Palm et al., "Neuronal Expression of Zinc Finger Transcription Factor REST/NRSF/XBR Gene," *The Journal of Neuroscience*, 18(4):1280-1296 (1998).

Pfeifer et al., "Delivery of the Cre recombinase by a self-deleting lentiviral vector: Efficient gene targeting in vivo," *Proc. Natl. Acad. Sci. USA*, 98(20):11450-11455 (2001).

Roopra et al., "Transcriptional Repression by Neuron-Restrictive Silencer Factor is Mediated via the Sin3-HIstone Deacetylase Complex," *Molecular and Cellular Biology*, 20(6):2147-2157 (2000).

Schoenherr et al., "Identification of potential target genes for the neuron-restrictive silencer factor," *Proc. Natl. Acad. Sci. USA*, 93:9881-9886 (1996).

Schoenherr et al., "Silencing is golden: negative regulation in the control of neuronal gene transcription," *Current Opinion in Neurobiology*, 5:566-571 (1995).

Timmusk et al., "Brain-derived Neurotrophic Factor Expression in Vivo is under the Control of Neuron-restrictive Silencer Element," *The Journal of Biological Chemistry*, 274(2):1078-1084 (1999).

Van Praag et al., "Functional neurogenesis in the adult hippocampus," *Nature*, 415:1030-1034 (2002).

Huang et al., "RNAa is Conserved in Mammalian Cells," *PLoS One* 5(1):e8848, 2010.

Li et al., "Small dsRNAs induce transcriptional activation in human cells," *Proc. Natl. Acad. Sci. USA* 103(46):17337-17342, 2006.

Janowski et al., "Activating gene expression in mammalian cells with promoter-targeted duplex RNAs," *Nat. Chem. Biol.* 3(3):166-173, 2007.

Rossi, "Transcriptional activation by small RNA duplexes," *Nat. Chem. Biol.* 3(3):136-137, 2007.

Alnylam Pharmaceuticals RNA activation webpage, as it appeared on Jun. 4, 2010 (http://www.alnylam.com/Leadership-in-RNAi/RNA-Opportunities/RNAa.php).

* cited by examiner

FIG. 9A

| # | ID | | | | | | | | |
|---|---|---|---|---|---|---|---|---|---|
| 1. | mCG1035220 | | 42 | 0.002 | GA_x6K02T2PVTD | | | | |
| 2. | mCG10137 | stathmin-like 2 | | 40 | 0.008 | GA_x6K02T2NDQK | | SCG10 PROTEIN | |
| 3. | mCG1035704 | | | 40 | 0.008 | GA_x54KRFPKRY5 | | | |
| 4. | mCG1035562 | | 40 | 0.008 | GA_x54KRFPKRY5 | | | | |
| 5. | mCG1035561 | | | 40 | 0.008 | | | | |
| 6. | mCG22243 | cholinergic receptor, nicotinic, beta polypeptide 2 (neuronal) | | | Chrnb2 | 40 | 0.008 | GA_x6K02T2P9AN | |

NEURONAL ACETYLCHOLINE RECEPTOR PROTEIN, BETA-2 CHAIN

| 7. | mCG22232 | | 40 | 0.008 | GA_x6K02T2P9AN | | NICE-5 E2 UBIQUITIN LIGASE | |
| 8. | mCG1032339 | | 40 | 0.008 | GA_x6K02T2P9AN | | |
| 9. | mCG1032259 | | 40 | 0.008 | GA_x6K02T2P9AN | | NOT ANNOTATED |
| 10. | mCG119968 | | 40 | 0.008 | GA_x6K02T2NNLH | | NOT ANNOTATED |
| 11. | mCG133869 | cyclin-dependent kinase 5, regulatory subunit 2 (p39) | | Cdk5r2 | 38 | 0.031 | GA_x54KRFPKRY5 | CYCLIN-DEPENDENT KINASE 5 ACTIVATOR 2 |

| 12. | mCG12300 | | 38 | 0.031 | GA_x6K02T2P8SN | | NOT ANNOTATED |
| 13. | mCG12306 | hairy and enhancer of split 3, (Drosophila) | Hes3 | 38 | 0.031 | GA_x6K02T2P8SN | |
| 14. | mCG1028003 | bHLH-PAS type transcription factor NXF | nxf | 38 | 0.031 | GA_x6K02T2QMRN | BASIC HELIX-LOOP-HELIX/PAS TRANSCRIPTION FACTOR |
| 15. | mCG133294 | | | | | | | |

| 16. | mCG6739 | histamine receptor H 3 | Hrh3 | 38 | 0.031 | GA_x6K02T2NK0G | HISTAMINE H3 RECEPTOR |
| 17. | mCG3401 | | 38 | 0.031 | | | |
| 18. | mCG1041396 | | 38 | 0.031 | | | |
| 19. | mCG1048109 | | 38 | 0.031 | GA_x6K02T2PG0R | | |
| 20. | mCG1043790 | | 36 | 0.12 | | | |
| 21. | mCG1027799 | | 36 | 0.12 | | | |
| 22. | mCG117430 | | 36 | 0.12 | GA_x6K02T2NLA8 | | NUCLEOLAR PHOSPHOPROTEIN P130-RELATED |
| 23. | mCG1047717 | | 36 | 0.12 | GA_x6K02T2R7CC | | CUTANEOUS T-CELL LYMPHOMA TUMOR ANTIGEN SE70-2 RELATED |
| 24. | mCG11586 | | 36 | 0.12 | GA_x6K02T2NR3J | | GALANIN RECEPTOR-RELATED |
| 25. | mCG22260 | G protein-coupled receptor 19 | Gpr19 | 36 | 0.12 | GA_x6K02T2NTSL | |
| 26. | mCG133959 | | 36 | 0.12 | GA_x6K02T2NUPS | | PLACENTAL RIBONUCLEASE INHIBITOR-RELATED |
| 27. | mCG23541 | | 36 | 0.12 | GA_x6K02T2NUPS | | |
| 28. | mCG23548 | | 36 | 0.12 | GA_x6K02T2NUPS | | |
| 29. | mCG23547 | par-6 (partitioning defective 6,) homolog alpha (C. elegans) | | Pard6a | 36 | 0.12 | GA_x6K02T2NUPS | PAR-6 RELATED |

| 30. | mCG23544 | | 36 | 0.12 | GA_x6K02T2NUPS | | POTASSIUM-CHLORIDE COTRANSPORTER SLC12A5-RELATED |
| 31. | mCG17512 | | 36 | 0.12 | GA_x6K02T2NGB1 | | UNCHARACTERIZED |
| 32. | mCG1113934 | | 36 | 0.12 | GA_x6K02T2NGB1 | | |
| 33. | mCG17563 | hyperpolarization-activated, cyclic nucleotide-gated K+ 3 | Hcn3 | 36 | 0.12 | GA_x6K02T2P9AN | HYPERPOLARIZATION ACTIVATED CYCLIC NUCLEOTIDE-GATED POTASSIUM CHANNEL |
| 34. | mCG17559 | CDC-like kinase 2 | Clk2 | 36 | 0.12 | GA_x6K02T2P9AN | CLK FAMILY (CMGC GROUP V) |
| 35. | mCG14692 | | 36 | 0.12 | GA_x6K02T2RBEM | | HEAVY NEUROFILAMENT SUBUNIT |
| 36. | mCG4646 | | 36 | 0.12 | GA_x6K02T2NCNC | | |
| 37. | mCG1028890 | | 36 | 0.12 | GA_x54KRFPKG5P | | REVERSE TRANSCRIPTASE-RELATED |
| 38. | mCG1038332 | | 36 | 0.12 | | Crhr2 | 36 | 0.12 | GA_x54KRFPKMMR | CORTICOTROPIN RELEASING FACTOR RECEPTOR 2 |
| 39. | mCG121588 | corticotropin releasing hormone receptor 2 | | | | | | |

FIG. 9B

| # | Gene ID | | Description | | | |
|---|---|---|---|---|---|---|
| 40. | mCG13931 | 34 | 0.49 | | | GA x6K02T2R7CC |
| 41. | mCG1047442 | 34 | 0.49 | | | GA x6K02T2R7CC |
| 42. | mCG19124 | 34 | 0.49 | | | GA x6K02T2QYV6 TUMOR SUPPRESSING SUBTRANSFERABLE CANDIDATE 1 |
| 43. | mCG133863 | crystallin, beta A2 Cryba2 | 34 | 0.49 | | GA x54KRFPKRY5 BETA CRYSTALLIN A2 |
| 44. | mCG133862 | regulated endocrine-specific protein 18 Resp18 | 34 | 0.49 | | GA x54KRFPKRY5 REGULATED ENDOCRINE SPECIFIC PROTEIN 18 |
| 45. | mCG133881 | ETS-domain transcription factor Pet-1 Pet-1 | 34 | 0.49 | | GA x54KRFPKRY5 RETROVIRAL INTEGRATION SITE PROTEIN FLI-1-RELATED |
| 46. | mCG2077 | solute carrier family 8 (sodium/calcium exchanger), member 2 Slc8a2 | 34 | 0.49 | | GA x6K02T2RHK3 SODIUM/CALCIUM EXCHANGER 2 SLC8A2-RELATED |
| 47. | mCG11733 | RIKEN cDNA 2510039O18 gene 2510039O18Rik | 34 | 0.49 | | GA x6K02T2P8SN |
| 48. | mCG1035801 | 34 | 0.49 | | | GA x6K02T2NUPS |
| 49. | mCG140739 | 34 | 0.49 | | | GA x6K02T2PN5H EPHRIN RECEPTOR |
| 50. | mCG15214 | 34 | 0.49 | | | GA x6K02T2NK0G UNCHARACTERIZED |
| 51. | mCG59574 | 34 | 0.49 | | | GA x6K02T2PQVR |
| 52. | mCG1030670 | 34 | 0.49 | | | GA x6K02T2PH54 |
| 53. | mCG1030423 | 34 | 0.49 | | | |
| 54. | mCG62369 | 34 | 0.49 | | | GA x6K02T2PH54 LEUCINE-RICH REPEAT PROTEIN-RELATED |
| 55. | mCG140354 | 34 | 0.49 | | | GA x6K02T2RBEM SEC14-RELATED |
| 56. | mCG6671 | 34 | 0.49 | | | GA x6K02T2PTC2 DOCK-1 |
| 57. | mCG124492 | 34 | 0.49 | | | GA x6K02T2PVTD NEUROTRIMIN |
| 58. | mCG48764 | 34 | 0.49 | | | GA x6K02T2PVTD SPERMIDINE SYNTHASE |
| 59. | mCG7471 | 34 | 0.49 | | | GA x6K02T2PVTD NOT ANNOTATED |
| 60. | mCG126202 | sodium channel, voltage-gated, type X, alpha polypeptide Scn10a | 34 | 0.49 | | VOLTAGE DEPENDENT SODIUM CHANNEL ALPHA SUBUNIT |
| 61. | mCG18748 | LIM homeobox protein 3 Lhx3 | 34 | 0.49 | | GA x6K02T2NLDC LIM/HOMEOBOX PROTEIN-RELATED |
| 62. | mCG18753 | cDNA sequence BC030934 BC030934 | 34 | 0.49 | | GA x6K02T2NLDC SULFHYDRYL OXIDASE |
| 63. | mCG20317 | calcium channel, voltage-dependent, N type, alpha 1B subunit Cacna1b | 34 | 0.49 | | GA x6K02T2NLDC VOLTAGE-DEPENDENT P/Q-TYPE CALCIUM CHANNEL ALPHA-1A |
| 64. | mCG9596 | 34 | 0.49 | | | GA x6K02T2NNLH |

TRANSCRIPTIONAL REGULATION OF GENE EXPRESSION BY SMALL DOUBLE-STRANDED MODULATORY RNA

This application claims the benefit of U.S. Provisional Application No. 60/474,422, filed May 29, 2003, and U.S. Provisional Application No. 60/553,791, filed Mar. 16, 2004, which are incorporated herein by reference.

This invention was made with government support under NIH-Ro1AG20938-02 awarded by the National Institutes of Health. The government may have rights in aspects of this invention.

BACKGROUND OF THE INVENTION

The present invention relates generally to molecular and developmental biology and more specifically to methods of modulating gene expression and influencing cellular differentiation.

The expression of cell type-specific genes depends on both positive and negative gene expression controls, which are implemented throughout the developmental history of cells. Numerous genetic studies have provided evidence that cell type-specific activators and repressors of gene expression are essential components of the process. In addition to the conventional transcription machinery, gene expression control by small non-coding RNAs, at the post-transcriptional step, also appears to be essential to the regulation of gene expression. Non-coding RNA genes, which produce transcripts, can function directly as structural, catalytic or regulatory RNAs, rather than expressed mRNAs that encode proteins. Plants, flies, worms, mice and humans harbor significant numbers of small RNAs likely to play regulatory roles. Although most of the identified non-coding RNAs have unknown function, their sequences are typically conserved among different species, and many have intriguing expression patterns in different tissues or stages of development, pointing towards a general role for non-coding RNAs in modulating gene expression during development, such as tissue-specific patterning and cell fate specification.

The mammalian nervous system is composed of a remarkable number of different types of neurons and glia. While it has become clear over the past several years that specific genes control cellular differentiation, the molecular mechanisms by which neuron-specific gene expression is regulated in the central nervous system remain a focus of study. The regulatory mechanisms of gene expression that determine a stem cell's fate with regard to giving rise to a particular lineage remain largely unknown. Genes involved in regulating mammalian neural differentiation are just beginning to be discovered. Some important regulators identified to date include NeuroD, NeuroM, neurogenin, and the neuron restrictive silencing factor (NRSF).

Many of the genes important for neuronal differentiation and maintenance contain neuron-restrictive silencer element/Repressor Element 1 (NRSE/RE1) sequence, which is recognized by the protein neuron-restrictive silencer factor (NRSF), also known as RE-1 silencing transcription factor (REST). The maintainance of neuronal gene repression in non-neuronal cells depends on the ability of NRSF/REST to bind the NRSE sequence. To repress gene expression, NRSF/REST recruits negative transcriptional regulators such as HDACs and methyl-DNA binding proteins. Multipotent adult neural stem cells switch from actively repressing neuron-specific genes in the "stem cell state" to actively expressing neuron-specific genes in the "differentiated state" allowing the cell to proceed to become a neuron, a process that involves de-repression in order to activate transcription of genes having an NRSE. The mechanisms controlling the switch from active transcriptiponal repression to de-repression of neuron-specific genes are of great significance to the determination of cell fate.

Given the cellular diversity of the nervous system and the complexity of the underlying genetic mechanism, the understanding and treatment of nervous system disorders presents a unique challenge. The elucidation of the mechanisms that regulate the development of the nervous system and ability to modulate the regulation of genes that coordinate nervous system development is an important goal and will provide valuable information regarding the the causes and potential treatments of neurological and neurodegenerative disorders.

Thus, there exists a need to understand the processes that orchestrate gene expression within regulatory networks that coordinate cellular processes such as differentiation; to elucidate the molecular components involved in these processes; and to develop therapeutic tools for influencing cellular processes such as neuronal differentiation. The present invention satisfies this need and provides related advantages as well.

BRIEF DESCRIPTION OF THE DRAWINGS

FIG. 1 shows identification of the NRSE dsRNA from adult hippocampal neuronal cells.

FIG. 2 shows that the NRSE dsRNA induces neuronal differentiation of progenitor cells.

FIG. 3 shows the effect of the NRSE dsRNA on the expression of neuron-specific genes containing the NRSE/RE1 DNA element.

FIG. 4C shows a results of a reporter assay for NRSE dsRNA function to convert NRSF/REST from a repressor to an activator using the GluR2 promoter-driven luciferase construct. Intact and mutated mGluR2-luciferase constructswere prepared and the level of luciferase activity driven by each promoter in the presence or absence of NRSE dsRNA expression was compared.

FIG. 5A shows the ribozyme (Rz) sequence designed to cleave the asNRSE RNA. FIG. 5B shows that cells with Rz cleaving NRSE RNAs showed strong anti-differentiation effects. FIG. 5C shows the effect of Rz on the NRSE dsRNA in each differentiation pathway. Cell type-specific promoter-based reporter assay was performed in HCN A94 cells.

FIG. 6A shows nuclear localization of the NRSE dsRNA in cells differentiating to neuron. FIG. 6B shows binding of the NRSE dsRNA to endogenous NRSF/REST protein. FIG. 6C shows an results of an EMSA of NRSF/REST protein against NRSE dsRNA and dsDNA. While the concentration of each nucleotide was fixed as 20 µM, protein amount was increased 2-fold by each lane depending on arrow direction.

FIG. 9 provides a table listing further genes that contain the NRSE motif and can be modulated via the invention methods.

SUMMARY OF THE INVENTION

Figure 1A:
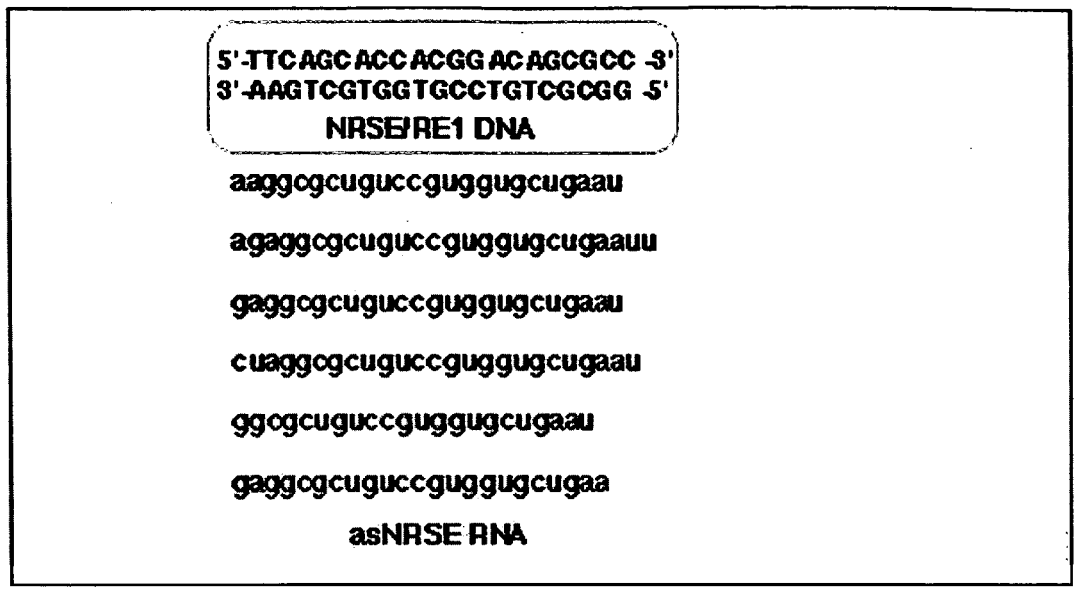
FIG. 1A shows the sequence that contained a match to the 21-nt NRSE/RE1 DNA sequence in the antisense orientation shown in pink.

The invention provides a method for modulating gene expression by contacting a cellular system with a double-stranded ribonucleic acid molecule capable of associating with the regulatory machinery that controls transcription of one or more genes, wherein the association results in altered expression of the one or more genes.

The invention is further directed to method for inducing the differentiation of neuronal stem cells into neurons by contacting a cellular system with a double-stranded ribonucleic acid molecule capable of associating with the regulatory machinery that controls transcription of one or more genes involved in neuronal differentiation and inducing neuronal differentiation.

In related embodiments, the invention provides particular compositions of ribonucleic acid molecules as well as therapeutic and screening applications of the invention.

DETAILED DESCRIPTION OF THE INVENTION

The invention is directed to small non-coding double-stranded ribonucleic acid (dsRNA) molecules, termed small modulatory RNAs (smRNAs), capable of coordinating the regulation of large clusters of genes, thereby mediating cellular processes, including, for example, cell fate determination, cell differentiation, maintenance of the differentiated state, cell motility, cellular functions and apoptosis. As described herein, one example of the coordination of cellular processes by an smRNA is the stimulation of neuronal development and functions, for example, ion channels, neurotransmitter receptors and their synthesizing enzymes, receptor-associated factors, neurotrophins, synaptic vesicle proteins, growth-associated, and cytoskeletal and adhesion molecule-factors involved in axonal guidance, transport machinery, transcription factors, and cofactors.

The invention also provides particular ribonucleic acid molecules that are capable of modulating gene expression through association with the regulatory machinery, that controls transcription of one or more genes. The invention is based, in part, on the discovery of a new class of functional non-coding RNAs, termed small modulatory RNAs (smRNAs), that have primary roles in regulating gene expression at the transcriptional level. Although distinct in function from small interfering RNA molecules (siRNAs), smRNAs have approximately the same nucleotide length (21-25 bp), enabling them to diffuse in cells without limitation. A smRNA of the invention can therefore be sequestered in specific cellular compartments and can, through interaction with one or more cognate protein partner(s), mediate effects in a spatial-temporal and sequence-dependent manner of target mRNA, DNA and proteins. In particular, the presence of small double-stranded ribonucleic acid molecules provided by the invention affects the activation of genes involved in coordinating complex cellular processes.

A small non-coding smRNA of the invention can orchestrate the interactions of a large number of genes within a network. Cellular processes too complex to be coordinated by a single gene can be orchestrated by a dsRNA as described herein. Such cellular processes encompass cell fate choices at any stage of development, including initial fate determinations, for example, from oocyte to embryonic stem cell as well as early differentiation into cell lineages such as formation of the inner cell mass (ICM) and trophoblast from blastomeres. Thus, in addition to the cellular processes described herein, the skilled person will appreciate that transcriptional regulation by a smRNA of the invention can orchestrate complex cellular processes, for example, cell fate determination, differentiation, lineage determination and organ development.

Therefore, while exemplified herein with regard to the NRSE/RE1 dsRNA and the regulation of neuronal gene expression through association with the NRSF/REST transcriptional machinery, the present invention is based on the broader discovery of dsRNA-dependent gene activation, previously thought to be limited to regulation by small interfering RNA (siRNA) molecules at a post-transcriptional level, at a transcriptional level. Those skilled in the art will appreciate that the ability of small non-coding dsRNA molecules to associate directly with proteins to regulate transcription of specific genes represnets a discovery that is universal to transcriptional regulation rather than one that is unique the nervous system as exemplified herein. Therefore, the skilled person will appreciate that the transcriptional regulation by a small non-coding dsRNA described by the invention is applicable to modulation of entire gene clusters that are interconnected in a network for controlling cellular processes as well as modulation of indvidual genes. Global regulation of gene expression, which depends on the interplay within a network of genes and is orchestrated by regulatory elements and their corresponding trans-acting facors, can be modulated with a small non-coding dsRNA as described herein.

In a particular embodiment, the invention is based, in part, on the discovery that small double-stranded ribonucleic acid molecules participate in the global orchestration of gene expression, for example, neuronal gene expression, during early eukaryotic development. The presence of small double-stranded ribonucleic acid molecules provided by the invention affects the activation of genes involved in cell fate determination and, ultimately, modulates cell differentiation.

As described herein, the small non-coding double-stranded ribonucleic acid molecules provided herein have a role in coordinating the regulation of both large gene clusters and individual genes by modulating gene expression. Consequently, a small non-coding double-stranded ribonucleic acid molecule of the invention can have a global effect on a gene network as well as a focused effect on expression of one or more individual genes. As described herein, a small non-coding double-stranded ribonucleic acid molecule of the invention can facilitate neuronal differentiation by modulating the expression of genes involved in the cell fate committment of neural stem cells early in development. As demonstrated in the Examples below qualitatively by immunostaining with lineage-specific markers and, quantitatively, with promoter-driven luciferase constructs, an NRSE dsRNAs can act as an inducer of neuronal differentiation. The introduction of an NRSE dsRNA alone can be sufficient to activate NRSE/RE1-containing neuron-specific genes and induce neuronal differentiation. Furthermore, as exemplified herein by showing that introduction of a ribozyme targeted against the NRSE dsRNA has anti-neuronal differentiation effects, an NRSE dsRNA is necessary to induce neuronal differentiation. The observations described herein gave rise to the discovery that small non-coding double-stranded ribonucleic acid molecules can act as key mediators of neuronal differentiation.

Figure 8:
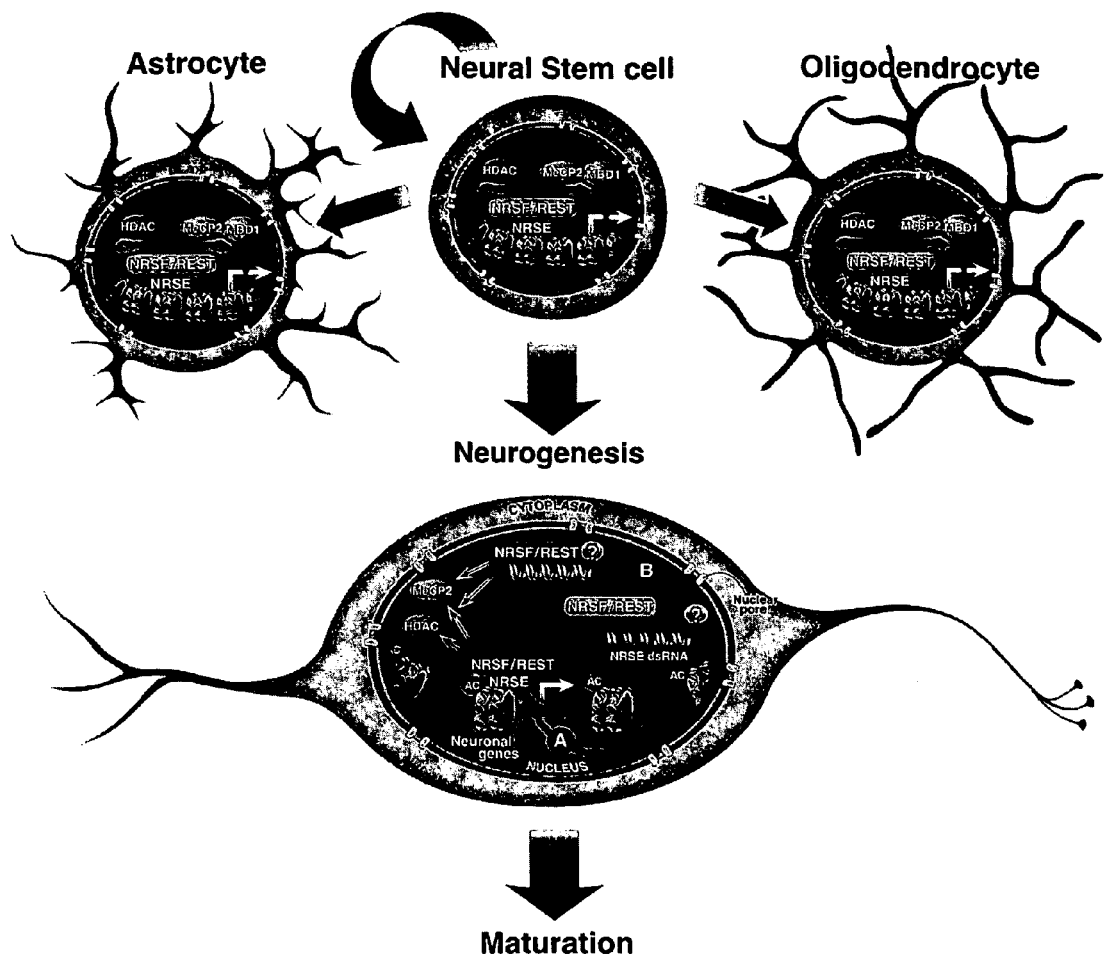
FIG. 8 is a schematic representation of activation events by the NRSE dsRNA. The NRSE dsRNA can trigger gene expression of neuron-specific genes through the association with NRSF/REST transcriptional machinery. This association results in NRSF/REST complex no longer binds to HDACs, MeCP2, and MBD1.

Multipotent neuronal stem cells require a highly selective gene regulation system to achieve uniquely different fates. As schematically depicted in FIG. 8, during the uncommitted stem cell state, the genes required for neural differentiation are repressed, while committing to the neural lineage requires repression of stem cell, astrocyte, oligodendrocyte lineages and de-repression of the neural restricted genes. By association with the regulatory machinery consisting of the NRSE/RE1 and NRSF/REST, the non-coding double-stranded ribonucleic acid molecules of the invention which correspond to NRSE sequences modulate the expression of NRSE element-dependent genes by switching the function of NRSF/REST between repressor and facilitator of gene expression.

In one embodiment, the invention is directed to a small double-stranded ribonucleic acid molecule termed neuron-restrictive silencer element/Repressor Element 1 double-stranded RNA, referred to throughout this disclosure interchangeably as NRSE/RE1 dsRNA or NRSE dsRNA. The sequence defined by this small non-coding dsRNA is derived from NRSE/RE1, which is recognized by NRSF/REST, known primarily as a negative transcriptional regulator that restricts neuronal gene expression to neurons. As described herein, the NRSE dsRNA can trigger gene expression of neuron-specific genes through association with the NRSF/REST transcriptional regulatory machinery.

As used herein, the term "regulatory machinery" refers a transcriptional machinery consisting of at least one nucleic acid regulatory element and at least one trans-acting regulatory protein that interact and, as a result of the interaction, modulate gene expression by controlling transcription. The regulatory machinery can control transcription by further recruitment, interaction or other association with co-factor modulatory proteins. Whether transcription of one or more genes is repressed or activated can depend on the particular set of co-factor modulatory proteins that is recruited by the regulatory machinery. As described herein, a smRNA of the invention can modulate gene expression by associating with the regulatory machinery through direct or indirect interaction with the either or both of the nucleic acid and protein components of the regulatory machinery.

In one embodiment, the regulatory machinery encompasses the NRSE/RE1 nucleic acid regulatory element and the NRSF/REST trans-acting regulatory protein. In this embodiment, co-factor modulatory proteins include the histone deacetylases, in particular HDAC1 and HDAC2, and methyl-CpG binding protein (MeCP2) which form a repressive chromatin state. As described in further detail below, the NRSE dsRNA provided by the present invention associates with the regulatory machinery that encompasses the NRSE/RE1 nucleic acid regulatory element and the NRSF/REST as the trans-acting regulatory protein.

This association, which is mediated through a dsRNA/protein interaction, results in the transition from neural stem cells with neuron-specific genes silenced by NRSF/REST, into cells of neuronal identity which can express neuronal genes. The apparent gene activation effects of the NRSE dsRNA clearly distinguish it from the post-transcriptional and target gene sequence-specific gene silencing effects of cellular interfering RNAs (miRNA/siRNAs), and demonstrate a previously unknown function for non-coding RNAs at a transcriptional level.

In one embodiment, the invention is thus directed to a double-stranded ribonucleic acid molecule termed neuron-restrictive silencer element/Repressor Element 1 double-stranded RNA (NRSE/RE1 dsRNA). The present invention also provides methods of modulating the expression of known genes or known nucleic acid sequences in eukaryotic cells using nucleic acid molecules capable of forming a double-stranded RNA.

The nucleic acid molecules provided by the present invention are capable of forming an NRSE/RE1 dsRNA that can bind to a portion of a genome, for example, to a nucleic acid regulatory element located in the promoter region of a particular gene. The nucleic acid molecules of the invention also are capable of binding to both endogenous as well as exogenous nucleic acid sequences. The nucleic acid sequences corresponding to an NRSE/RE1 smRNA of the invention can be encoded by one or more nucleic acid molecules, the expression of which results in the ribonucleic acid sequences capable of forming the smRNA of the invention.

The present invention therefore relates to ribonucleic molecules capable of forming an NRSE/RE1 dsRNA, to DNA molecules encoding the ribonucleic acid molecules capable of forming a dsRNA, to vectors and cells encompassing these molecules, to compositions encompassing the molecules and vectors, and to prophylactic and therapeutic methods for administering the ribonucleic acid molecules, the deoxyribonucleic molecules and the dsRNA.

As described herein, the nucleic acid molecules and methods provided by the invention have numerous uses for mediating cellular processes, including, for example, cell fate determination, cell differentiation, maintenance of the differentiated state, cell motility, cellular functions and apoptosis. As described herein, one example of the coordination of cellular processes by a small non-coding dsRNA is neuronal development and functions, for example, ion channels, neurotransmitter receptors and their synthesizing enzymes, receptor-associated factors, neurotrophins, synaptic vesicle proteins, growth-associated, and cytoskeletal and adhesion molecule-factors involved in axonal guidance, transport machinery, transcription factors, and cofactors. It is understood that the NRSE dsRNA is one example of a small non-coding dsRNA and the NRSE is likewise one example of a nucleic acid regulatory element from which a smRNA of the invention can be derived. Those skilled in the art will appreciate that many small non-coding dsRNAs derived from different nucleic acid regulatory elements exist, which coordinate numerous cellular processes.

As a consequence of their capability to modulate gene expression, the small non-coding smRNA of the invention are useful for treating or inhibiting the onset of disorders characterized by suppression of expression of particular genes involved in cellular processes, for example, neuronal differentiation. In particular, the NRSE/RE1 smRNA of the invention has therapeutic utility for conditions characterized by aberrances in neuronal stem cell differentiation and morphogenesis.

In the central nervous system, the neuron-restrictive silencer factor (NRSF), also known as RE-1 silencing transcription factor (REST) plays a critical role as a key transcriptional repressor for neuron-specific genes in non-neuronal cells as described by Chen et al., *Nature Genetics* 20:136-42 (1998); Huang et al., *Nature Neuroscience* 2:867-72 (1999); Lunyak et al., *Science* 298:1747-52 (2002); Palm et al., *Journal of Neuroscience* 18:1280-96 (1998); Schoenherr and Anderson, *Current Opinions in Neurobiology* 5:566-71 (1995b); Schoenherr et al., *Proc Natl Acad Sci USA* 93:9881-6 (1996), each of which is incorporated herein by referewnce in its entirety. NRSF/REST is a krüppel family zinc finger protein and binds specifically to a 21- to 23-base pair (bp) conserved DNA response element (NRSE/RE1). NRSE/RE1 sequences are encoded within a broad range of genes involved in neuronal development and function, including ion channels, neurotransmitter receptors and their synthesizing enzymes, receptor-associated factors, neurotrophins, synaptic vesicle proteins, growth-associated, and cytoskeletal and adhesion molecule-factors involved in axonal guidance, transport machinery, transcription factors, and cofactors. The consensus NRSE/RE1 sequence is conserved between *Xenopus*, mouse, rat, chicken, sheep, and human.

The maintenance of neuronal gene repression in non-neuronal cells depends on the ability of NRSF/REST to bind the NRSE sequence. NRSF/REST mediates transcriptional repression through the association of the N-terminal repressor domain with the mSin3/histone deacetylase-1/2 (HDAC1/2) complex and through the association of C-terminal repressor domain with the CoREST complex by recruitment of MeCP2 or HDACs as described by Andres et al., *Proc Natl Acad Sci USA* 96:9873-8 (1999); Grimes et al., *J Biol Chem* 275:9461-7 (2000); Huang et al., supra, 1999; Lunyak et al., supra, 2002; Naruse et al., *Proc Natl Acad Sci USA* 96:13691-6 (1999); Roopra et al., *Mol Cell Biol* 20:2147-57 (2000), each of which is incorporated herein by referewnce in its entirety.

As described herein, the NRSF is a flexible mediator of NRSE regulatory elements. An NRSE smRNA of the invention can interact with the NRSF and exploit the role of the NRSF as a mediator of gene rexpression by causing the NRSF to switch co-factors from repressors to activators. In certain embodiments, the NRSF represents a vertebrate silencer protein that regulates a large battery of cell type-specific genes, and therefore can function as a master negative regulator of neurogenesis. Several of the genes containing the NRSE are essential for establishment and maintenance of the neuronal phenotype; these include neuron-specific cytoskeletal proteins, neurotransmitters and their biosynthetic enzymes, synaptic vesicle components, neurotrophins, and cell adhesion molecules. Perturbation of REST expression and function results in cellular apoptosis, aberrant differentiation and morphogenesis, and lethality, a further indication that NRSF function is essential for normal embryogenesis.

In one embodiment, the invention provides an isolated double-stranded nucleic acid molecule encompassing a first ribonucleic acid molecule having a sequence set forth as SEQ ID NO: 1 and a second ribonucleic acid molecule having a sequence corresponding to the complement of said first nucleic acid molecule. The nucleic acid molecule designated SEQ ID NO: 1 corresponds to the 5' to 3' strand of the NRSE dsRNA (see FIG. 3C) and has the sequence 5'-UUCAGCAC-CACGGACAGCGCC-3'. In this embodiment of the invention, the nucleic acid complex corresponds to an intermolecular NRSE/RE1 dsRNA that is formed from two distinct ribonucleic acid molecules having complementary sequences. The dsRNA can be formed within a cell upon introduction, or the dsRNA can be introduced into a cell as a preformed complex.

The term "nucleic acid molecule," as used herein, refers to an oligonucleotide or polynucleotide of natural or synthetic origin, including analogs such as peptide nucleic acids. A nucleic acid molecule can be single- or double-stranded genomic DNA, cDNA or RNA, and can represent the sense strand, the antisense strand, or both. A "nucleic acid complex," as used herein refers more specifically to a double-stranded nucleic acid molecule formed by intermolecular bonds between complementary bases. A nucleic acid molecule can include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a nucleic acid molecule is desired, for example, where a nucleic acid molecule of the invention is used to screen for promoter responsive elements.

The term "double-stranded ribonucleic acid molecule" or "dsRNA" refers specifically to a nucleic acid complex consisting of two complementary strands corresponding to a first and a second ribonucleic acid sequence that can have, for example, between 14 and 26 contiguous nucleotides per strand, between 15 and 25, between 16 and 24, between 17 and 23, between 18 and 22, between 19 and 21 contiguous nucleotides per strand. The term encompasses both partially or completely double-stranded molecules. A nucleic acid molecule of the invention can be a double-stranded ribonucleic acid molecule that includes a portion of sequence substantially identical to a portion of a non-coding, nucleic acid regulatory element corresponding to one or more genes, except for possessing Uracil instead of Thymine. The nucleic acid regulatory element can embedded at any location with in the genome, for example, in the promoter, intron, exon, 3' UTR, or 6' UTR.

A nucleic acid molecule comprising a double-stranded ribonucleic acid can be formed from a single nucleic acid molecule that contains the first and second ribonucleic acid sequences separated by a spacer sequence. In this embodiment of the invention, the transcription of the two ribonucleic acid sequences can be driven by a single promoter and the nucleic acid sequences are separated by a short spacer sequence. The spacer sequence can be of any length desired by the user, and can have for example, 2 or more, 3 or more, 4 or more, 5 or more, 6 or more, 7 or more, 8 or more 9 or more, 10 or more, 15 or more, 20 or more, 25 or more, 30 or more, 40 or more nucleotides. The sequence of the spacer can be selected based on the sequence and length of the dsRNA. For a smRNA of the invention a spacer sequence can have any length and sequence that facilitates formation of a functional dsRNA including, for example, seven nucleotides having the sequence TCAAGAG, or four nucleotides having the sequence TAAA. It is understood that depending on the sequence of dsRNA and the possible structure, the both the length and sequence of the spacer can be adjusted. If desired, the spacer sequence can further modified to include regulatory elements useful for expression. Upon expression, the resulting transcript folds back on itself to form a dsRNA stem-loop, also referred to as hairpin, structure based upon complementary base pairing of the first ribonucleic acid sequence and the second ribonucleic acid sequence, which is its reverse complement.

In a related embodiment, the two ribonucleic acid sequences are expressed off separate promoters rather than a single promoter and the term double-stranded ribonucleic acid molecule refers to a short nucleic acid complex consisting of the first ribonucleic acid sequence and a second ribonucleic acid sequence, which is its complement.

The term "isolated" in reference to a nucleic acid molecule is intended to mean that the molecule is substantially removed or separated from components with which it is naturally associated, or otherwise modified by a human hand, thereby excluding nucleic acid molecules as they exist in nature. An isolated nucleic acid molecule of the invention can be in solution or suspension, or immobilized on a filter, glass slide, chip, culture plate or other solid support. The degree of purification of the nucleic acid molecule, and its physical form, can be determined by those skilled in the art depending on the intended use of the molecule.

The term "comprising" or "containing" in reference to a nucleic acid molecule of the invention, is intended to mean that the nucleic acid molecule can contain additional nucleic acid sequences at either the 5' or 3' end of the recited sequence, or branching from an internal position within the recited sequence. The additional nucleotide sequences can, if desired, correspond to naturally occurring sequences, including promoter sequences, coding or non-coding sequences, or other untranslated regions. Alternatively, the additional nucleotide sequence can correspond to a spacer sequence that allows the first and second nucleic acid sequences to fold over in a hairpin structure so as to align by complementary base pairing. The additional sequences also can correspond to sites useful in cloning applications; to vector sequences or other nucleic acid sequences that can be useful in gene expression. Those skilled in the art can determine appropriate sequences flanking the recited nucleotide sequences for a particular application of the method.

In a further embodiment, the invention provides an isolated nucleic acid molecule encompassing a ribonucleic acid sequence set forth as SEQ ID NO: 1. The nucleic acid molecule designated as SEQ ID NO: 1 corresponds to the 5' to 3' strand of the double-stranded NRSE/RE1 ribonucleic acid molecule provided by the invention.

In a further related embodiment, the invention provides an isolated nucleic acid molecule encompassing a first ribonucleic acid sequence set forth as SEQ ID NO: 1 and a second ribonucleic acid sequence corresponding to the reverse complement of said first ribonucleic acid sequence, wherein the first and second ribonucleic acid sequences are separated by a short spacer sequence. In this embodiment, an intramolecular NRSE/RE1 dsRNA is formed from a single, linear ribonucleic acid molecule that corresponds to the isolated nucleic acid molecule. Thus, the nucleic acid molecule of this embodiment can be depicted as follows: UUCAGCAC-CACGGACAGCGCC-SPACER-AAGUCGUGGUGCCU-GUCGCGG.

As used herein, the term "reverse complement" when used in reference to a first nucleic acid sequence refers to the complementary sequence of the first nucleic acid sequence as dictated by base-pairing, but in reverse orientation so as to result in complementarity upon fold-over into a hairpin structure. The term encompasses partial complementarity where only some of the bases are matched according to base pairing rules as well as total complementarity between the two nucleic acid sequences. The degree of complementarity between the first and second nucleic acid sequences can have significant effects on the stability and efficiency of the dsRNA.

In contrast, a complement of a first nucleic acid molecule in embodiments where an intermolecular dsRNA is formed from two distinct ribonucleic acid refers to the complementary sequence as dictated by base-pairing. A second nucleic acid sequence corresponding to the complement of the first nucleic acid sequence is present in those embodiments of the invention where the nucleic acid sequences are not expressed from a single transcriptional unit and, consequently, do not fold over into a hairpin structure. Rather, the two physically distinct molecules align and form intermolecular bonds as dictated by base complementarity.

The terms "double-stranded ribonucleic acid" and "dsRNA" can be used interchangeably and both refer to a short duplex consisting of a first and a second nucleic acid sequence. The term includes intramolecular dsRNAs formed from a single, linear ribonucleic acid molecule as well as intermolecular dsRNAs formed from two disctinct molecules. Stated differently, the double-stranded molecule can be formed by a single self-complementary RNA strand where one sequence is the reverse complement of the second sequence strand or two complementary RNA strands. RNA duplex formation may be initiated either inside or outside the cell. The nucleic acid molecule may be introduced in an amount that allows delivery of at least one copy per cell. Higher doses, for example, at least 5, 10, 100, 500 or 1000 copies per cell of double-stranded material can also be introduced and can allow for more efficient modulation of gene expression, while lower doses can be useful for specific applications.

Modulation of gene expression is sequence-specific in that the dsRNA sequence corresponds to a particular nucleic acid regulatory element, for example, a promoter regulatory element, that regulates expression of a specific gene. In particular, a NRSE/RE1 dsRNA molecule provided by the present invention recognizes and binds to a sequence-specific motif or region located in the promoter region of particular genes and modulates gene expression by interfering with the suppression of transcription. A smRNA of the invention can associate with a promoter regulatory element, for example, the NRSE/RE1. Modulation of gene expression by a dsRNA of invention can occur in several distinct ways. In particular, a smRNA of the invention can modulate gene expression by altering the interaction between a trans-acting protein and a nucleic acid regulatory element resulting, for example, in a shift from transcriptional repression to de-repression.

Figure 4B:
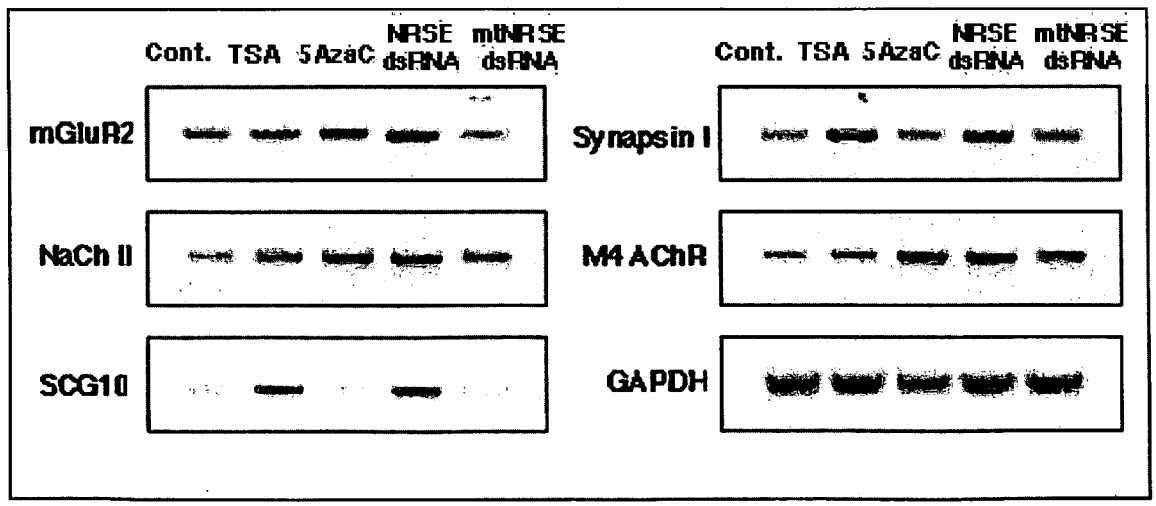
FIG. 4B shows RT-PCR analysis of NRSE/RE1 containing genes in HCN A94 cells. Cells were treated with either an HDAC inhibitor trichostatin A (TSA) or with de-methylation reagent 5'-aza-cytidine (5AzaC).
Figures 4, 4A:
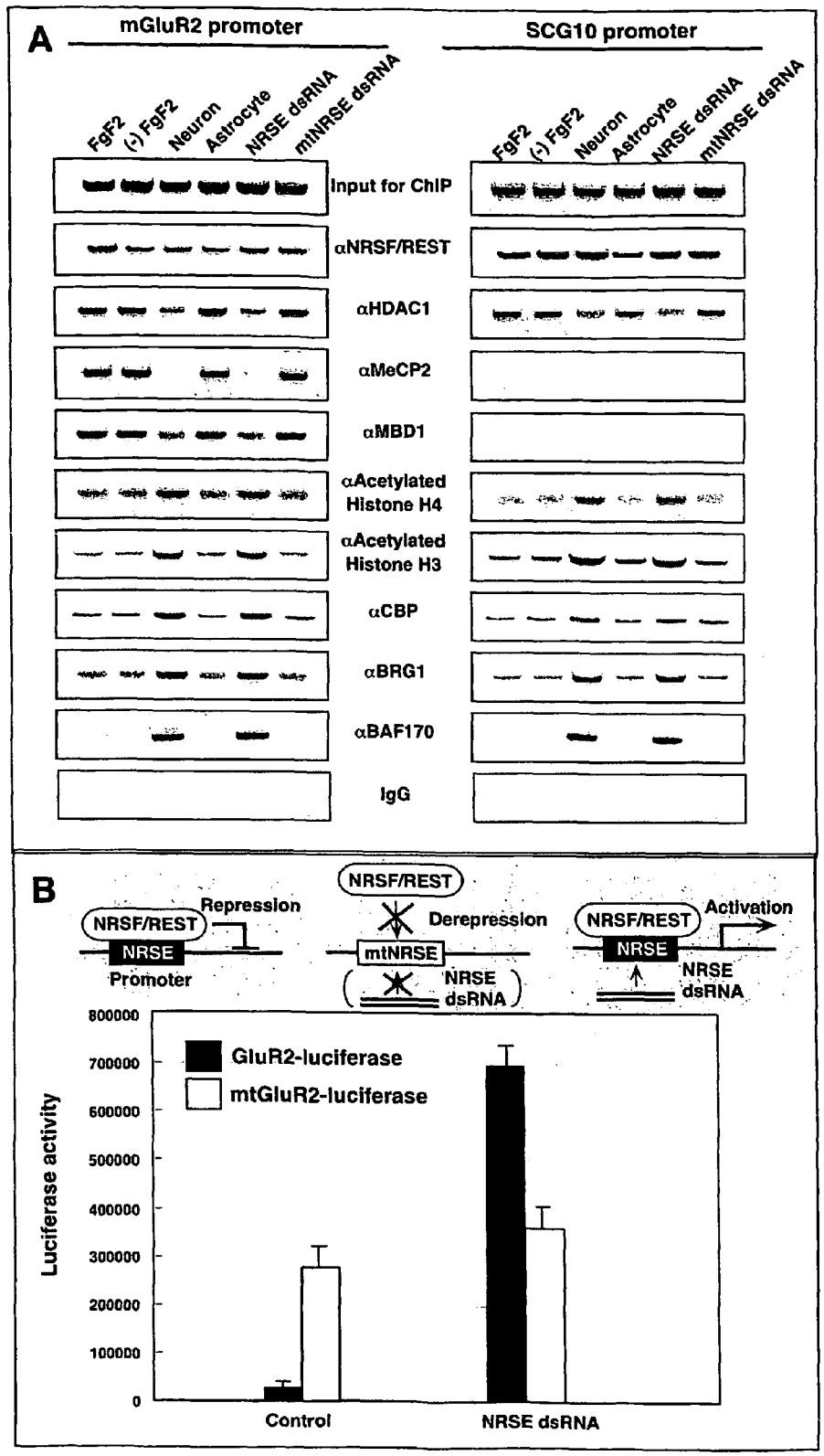
FIG. 4 shows NRSE dsRNA-directed chromatin changes of NRSE/RE1 containing genes.
FIG. 4A shows a chromatin immunoprecipitation (ChIP) assay for chromatin regulating factors.

As shown in FIG. 4, the NRSF/REST trans-acting protein remains stably associated with the NRSE/RE1 nucleic acid regulatory element in both the repressed stem cell state, as well as during differentiated states that require dsRNA dependent de-repression. The NRSE chromatin changes from a repressed state characterized by the association between the NRSF with co-factor modulatory proteins including, HDACs, MBD1 and MeCP2 to an activated state where the NRSF associates with a distinct set of modulatory proteins, in particular, acetylated histones, does not involve a change in the association of the NRSF/REST protein itself. Thus, the change in NRSF/REST function is not necessarily a consequence of physical severance from the NRSE/RE1, but rather can be a consequence of the association, in this particular embodiment through physical interaction, between the NRSE smRNA of the invention and the NRSF/REST trans-acting regulatory protein. As a result of the interaction between a dsRNA and the NRSF/REST trans-acting regulatory protein, the NRSF/REST can switch cofactors from repressors to activators or vice versa. Thus, a smRNA of the invention can be useful to exploit the intrinsic ability of the NRSF/REST to function as a flexible mediator of NRSE regulatory elements and indirectly serve as an activator as well as an inhibitor of gene expression.

In the absence of an NRSE/smRNA of the invention, NRSE/RE1-containing neuronal genes are actively repressed by the NRSF/REST machinery through the association of HDACs and MBD-binding proteins. At the onset of neuronal induction, the dsRNA interacts directly with the NRSE/RE1/NRSF/REST regulatory machinery on the genome, and triggers an organizational change in transcriptional activation (FIG. 8). A smRNA of the invention also can act through physical association with the NRSF/REST and alter NRSF/REST function by inducing a conformational change. Through both modes of modulation, a NRSE smRNA of the invention alleviates transcriptional repression that results from the association between the NRSF/REST trans-acting protein with co-factor modulatory proteins, including, for example, HDACs, MeCP2, and MBD1.

Generally, a dsRNA encompasses fragments of at least 18, at least 19, at least 20, at least 21, at least 22, at least 23, at least 24, at least 25, at least 30, at least 35, at least 40, at least 45, at least 50 or more nucleotides per strand, with characteristic 3' overhangs of at least 1, at least 2, at least 3, or at least 4 nucleotides. As set forth above, a double-stranded RNA molecule can be of any length desired by the user as long as the ability to modulate gene expression is preserved. The ribonucleic acid molecules can correspond to strands that are polyadenylated.

A nucleic acid molecule or complex can be synthesized either in vivo or in vitro. Endogenous RNA polymerase of the cell can mediate transcription in vivo; or cloned RNA polymerase can be used for transcription in vivo or in vitro. For transcription from a transgene in vivo or an expression construct, a regulatory region such as, for example, a promoter, enhancer, silencer, splice donor and acceptor can be used to transcribe the ribonucleic acid strand or strands. Modulation can be targeted by specific expression in an organ, tissue, or cell type; stimulation of an environmental condition, for example, infection, stress, temperature, chemical inducers; and/or engineering transcription at a developmental stage or age.

A nucleic acid molecule of the invention can be chemically or enzymatically synthesized by manual or automated reactions. An NRSE/RE1 dsRNA can be synthesized by a cellular RNA polymerase or a bacteriophage RNA polymerase, for example, T3, T7, SP6. The use and production of an expression construct are known in the art as described, for example, by Goeddel, *Gene Expression Technology*, Academic Press, 1990; Kriegler, *Gene Transfer and Expression*, Stockton Press, 1990; Murray, *Gene Transfer and Expression Protocols*, Humana Press, 1991; WO 97/32016; U.S. Pat. Nos. 5,593,874, 5,698,425, 5,712,135, 5,789,214, and 5,804,693; and the references cited therein.

If synthesized chemically or by in vitro enzymatic synthesis, the RNA can be purified prior to introduction into the cell. For example, RNA can be purified from a mixture by extraction with a solvent or resin, precipitation, electrophoresis, chromatography, or a combination thereof. Alternatively, the RNA can be used with no or a minimum of purification to avoid losses due to sample processing. The RNA can be dried for storage or dissolved in an aqueous solution. The solution can contain buffers or salts to promote annealing, and/or stabilization of the duplex strands.

A nucleic acid molecule of the invention can be directly introduced into the cell (intracellularly); or can be introduced extracellularly into a cavity, interstitial space, into the circulation of an organism, introduced orally, or can be introduced by immersing an organism in a solution containing the nucleic acid.

Physical methods of introducing a nucleic acid molecule, for example, injection directly into the cell or extracellular injection into the organism, can also be used. Vascular or extravascular circulation, the blood or lymph system, the phloem, the roots, the embryonic fluid and the cerebrospinal fluid are sites where the RNA can be introduced. Furthemore, a transgenic organism that expresses a NRSE/RE1 dsRNA from a recombinant construct can be produced by introducing the construct into a zygote, an embryonic stem cell, or another multipotent cell derived from the appropriate organism.

A promoter useful in the present invention can comprise a promoter of eukaryotic or prokaryotic origin that can provide high levels of constitutive expression across a variety of cell types and will be sufficient to direct the transcription of a distally located sequence, which is a sequence linked to the 5' end of the promoter sequence in a cell. The promoter region can also include control elements for the enhancement or repression of transcription and can be modified as desired by the user and depending on the context. Suitable promoters include, for example, RNA polymerase (pol) III promoters including, but not limited to, the human and murine U6 pol III promoters as well as the human and murine H1 RNA pol III promoters; RNA polymerase (pol) II promoters; cytomegalovirus immediate early promoter (pCMV), the Rous Sarcoma virus long terminal repeat promoter (pRSV), and the SP6, T3, and T7 promoters. In addition, a hybrid promoter also can be prepared that contains elements derived from, for example, both a RNA polymerase (pol) III promoter and an RNA polymerase (pol) II promoter. Modified promoters that contain sequence elements derived from two or more naturally occurring promoter sequences can be combined by the skilled person to effect transcription under a desired set of conditions or in a specific context.

Enhancer sequences upstream from the promoter or terminator sequences downstream of the coding region can optionally be included in a vector for expression of a dsRNA of the present invention to facilitate expression. Vectors useful for expression of a dsRNA of the present invention can also contain additional nucleic acid sequences, such as a polyadenylation sequence or a localization sequence. Such additional sequences can be inserted into the vector such that they are operably linked with the promoter sequence, if transcription is desired. Alternatively, the inserted sequences can be placed at any position in the vector.

An inducible promoter also can be useful for expressing a smRNA of the invention. An inducible promoter is transcriptionally active when bound to a transcriptional activator, which in turn is activated under a specific set of conditions, for example, in the presence of a particular combination of chemical signals that affect binding of the transcriptional activator to the inducible promoter and/or affect function of the transcriptional activator itself. Thus, an inducible promoter is a promoter that, either in the absence of an inducer, does not direct expression, or directs low levels of expression, of a nucleic acid sequence to which the inducible promoter is operably linked; or exhibits a low level of expression in the presence of a regulating factor that, when removed, allows high-level expression from the promoter, for example, the tet system. In the presence of an inducer, an inducible promoter directs transcription at an increased level.

The function of a promoter can be further modified, if desired, to include appropriate regulatory elements to provide for the desired level of expression or replication in the host cell. For example, appropriate promoter and enhancer elements can be chosen to provide for constitutive, inducible or cell type-specific expression. Useful constitutive promoter and enhancer elements for expression of a smRNA of the invention can include, for example, RSV, CMV, CAG, SV40 and IgH elements. Other constitutive, inducible and cell type-specific regulatory elements are well known in the art.

A promoter that is particularly useful in a lentiviral vector is compatible with mammalian genes and, further, can be compatible with expression of genes from a wide variety of species. For example, a promoter useful for practicing the invention can be a promoter of the eukaryotic RNA polymerases pol II and pol III, or a hybrid thereof. The RNA polymerase III promoters have a transcription machinery that is compatible with a wide variety of species, a high basal transcription rate and recognize termination sites with a high level of accuracy. For example, the human and murine U6 RNA polymerase (pol) III and H1 RNA pol III promoters are well characterized and useful for practicing the invention. As exemplified below, because the activities of these two promoters as well as the localization of expressed nucleic acid sequences can vary from cell type to cell type, if desired, U6 and H1 lentiviral vectors can be prepared and targeted to the desired cells for modulation of the expression of one or more genes. One skilled in the art will be able to select and/or modify the promoter that is most effective for the desired application and cell type so as to optimize modulation of the expression of one or more genes.

Thus, promoters that are useful in the invention include those promoters that are sufficient to render promoter-dependent gene expression controllable for cell-type specificity, cell-stage specificity, or tissue-specificity, and those promoters that are inducible by external signals or agents. The promoter sequence can be one that does not occur in nature, so long as it functions in a mammalian cell.

As used herein, the term "in vivo" means an environment within a living organism or living cell. Such a living organism can be, for example, a multi-cellular organism such as a rodent, mammal, primate or human or another animal such as an insect, worm, frog or fish, or a uni-cellular organism such as a single-celled protozoan, bacterium or yeast. The cell can be in an in utero animal, or in an ex utero animal. Both living cells derived from an organism and used directly (primary cells) as well as cells grown for multiple generations or indefinitely in culture are encompassed within the term "in vivo" as used herein. As an example, an oocyte removed from an organism such as a mouse or a frog and used directly or grown in a tissue culture dish constitutes an in vivo environment. In vivo applications of the invention include applications in which a ribonucleic acid molecule of the invention is introduced, for example, into a mammalian, primate, human, murine, porcine, bovine, yeast or bacterial cell, as well as into a mammalian fertilized oocyte, a mammalian embryonic or neuronal stem cell.

As used herein, the term "in vitro" means an environment outside of a living organism or cell. Applications performed, for example, in a microfuge tube, or a 96, 384 or 1536 well plate, or another assay format with purified or partially purified proteins or cellular extracts outside of a living organism are in vitro applications. Thus, applications performed using whole-cell or fractionated extracts derived from lysed cells, or performed with reconstituted systems, are encompassed within the term "in vitro" as used herein.

As used herein, the term "vector" refers to one or more nucleic acid molecules capable of transporting another nucleic acid sequence, for example, a ribonucleic acid sequence encompassing a first and second nucleic acid sequence, to which it has been linked. The term is intended to include any vehicle for delivery of a nucleic acid, for example, a virus, plasmid, cosmid or transposon. The term also encompasses vector systems of one or more physically separate vectors, for example, third-generation retroviral vector systems where the nucleic acid sequences encoding polypeptides having virus packaging functions necessary for generation of a retroviral vector of the invention can be divided onto separate expression plasmids that are independently transfected into the packaging cells.

The invention also provides a method for modulating gene expression by contacting a cellular system with a double-stranded ribonucleic acid molecule, wherein the double-stranded ribonucleic acid molecule is capable of associating with a regulatory machinery that controls transcription of one or more genes, and wherein the association results in altered expression of these one or more genes.

The cellular system in which the modulation of gene expression is effected using a smRNA of the invention can be an in vitro or in vivo. For example, modulation of gene expression by a smRNA of the invention can be assayed in vitro, for example, to confirm or maximize modulatory activity and efficiency of the dsRNA. Depending on the assay, quantitation of the amount of gene expression allows one to determine a degree of modulation in the presence of a smRNA of the invention, which can be an increase or decrease in gene expression of greater than 10%, 33%, 50%, 90%, 95% or 99% as compared to a cell not contacted. Lower doses of injected and longer times after administration of dsRNA can result in modulation of gene expression in a smaller fraction of cells, for, at least 10%, 20%, 50%, 75%, 90%, or 95% of targeted cells.

Quantitation of gene expression in a cell can be measured by detection of a gene product produced by the modulated gene as well as, indirectly, by measuring phenotypic changes associated with expression of the gene product. For example, the amount of gene product in the cell can be detected with a hybridization probe having a nucleotide sequence, or translated polypeptide can be detected with an antibody raised against a polypeptide epitope. In addition, a phenotypic change associated with expression of the gene can be measured, for example, cell type differentiation. In order to measure modulation of gene expression with a NRSE/RE1 ds RNA it can be useful to detect the differentiation of neuronal stem cells into neuronal cells. Differentiation into neuronal cells can be detected by a variety of techniques and assays known in the art and exemplified herein, for example, by ascertaining the presence of certain characteristics associated with neuronal cells including morphology as well as the presence of particular neuronal cell surface markers.

The one or more genes whose expression is modulated can be genes that have a pleiotropic effect. As used herein, the phrase "pleiotropic effect" refers to downstream regulation by one gene product of two or more genes so as to effect a number of features, characteristics or phenotypes. Significantly, two neuronal transcription factor genes contain the NRSE in their regulatory region, demonstrating the indirect effect on downstream genes. Neuronal cell fate determination involves the activation of a number of genes NRSE-containing genes that are essential for establishment and maintenance of the neuronal phenotype including, for example, neuron specific cytoskeletal proteins, neurotransmitters and their biosynthetic enzymes, synaptic vesicle components, neurotrophins, and cell adhesion molecules. Global regulation of neuronal gene expression, which depends on the interplay within a network of neuron-specific genes, is thus orchestrated by the NRSE/NRSF regulatory machinery and can be modulated with a NRSE/RE1 smRNA of the invention.

A variety of vectors can be utilized to deliver a double-stranded nucleic acid molecule to a cellular system. As used herein, the term "vector" refers to a nucleic acid molecule capable of transferring another nucleic acid sequence to which it has been linked. The term is intended to include any vehicle for delivery of a nucleic acid, for example, a virus, plasmid, cosmid or transposon.

Modulation of gene expression with a smRNA of the invention capitalizes on the discovery disclosed herein that presence of a dsRNA can affect the nature of the interaction of a nucleic acid regulatory element with a trans-acting protein. As described herein, a smRNA of the invention can be an inhibitor as well as an activator of gene expression based on the particular regulatory element and co-factor modulatory proteins recruited. The association between the dsRNA and the components of regulatory machinery can be a direct physical association as well as an indirect association, for example, through an intermediate molecule. While exemplified herein with regard to the promoter regulatory element (PRE) known as NRSE/REST, which is bound by the trans-acting protein NRSF, resulting in repression of neuronal gene transcription, the skilled person will appreciate the disclosure of a global dsRNA-mediated mechanism of regulating gene transcription that has broad applicability to cellular processes. In particular, the ability of dsRNA molecules of the invention to recognize specific regulatory sequences or motifs and associate with such regulatory sequences and their corresponding trans-acting proteins to globally regulate gene expression during cell fate determination is not spefific to neuronal cell differentiation as evidence by the presence of functional NRSEs in non-neuronal genes as described by Schoenherr et al., *Procl. Natl. Acad. Sci. USA* 93(18): 9881-9886 (1996). In this regard, the differences in responses among neuronal genes described herein (FIG. 4) further demonstrate the diversity among the REST/NRSF regulatory machinery and the responses, despite being generated by a common elemental-directed regulator (NRSE/NRSF), can vary based on expression timing, tissue and age dependency, maturation and/or each selective subtype of neurons.

In the absence of the smRNA of the invention, a lack of activation of neuron-specific genes occurs in neuronal stem cells as a result of NRSF binding to the NRSE and, ultimately, neuronal differentiation potency is lost, resulting in the neuronal stem cells remaining at the progenitor stage. This lack of activation of neuron-specific genes in the absence of an invention dsRNA can be attributed to the recruitment by the NRSE-bound NRSF of histone deacetylases (HDACs) and particular co-factor modulatory proteins, including, methyl-CpG binding proteins (MeCPs) and methyl-CpG binding domain proteins (MBDs), which mediate transcriptional repression by binding methylated nucleic acid sequences in a sequence specific manner.

In the absence of an smRNA of the invention, co-factor modulating proteins including, methyl-CpG binding proteins (MeCPs) and methyl-CpG binding domain proteins (MBDs), mediate transcriptional repression by associating with additional modulating proteins, for example, members of the Sin3 and histone deactylase protein families. As a consequence of the particular set of co-factor modulatory proteins that is thus recruited, transcription of one or more genes specific to expression in the nervous system is repressed. In the presence of an invention dsRNA, transcriptional repression can be relieved through several mechanisms. First, the presence of an invention dsRNA can effect a conformational change in the NRSF/NRSE complex that prevents association with the HDACs and associated binding proteins or other modulatory proteins that are part of the NRSE/REST machinery. Second, the presence of an invention dsRNA can result in a switch in the function of the NRSE/REST complex from transcritional repressor to enhancer by affecting the choice of co-factors or modulatory proteins that make up the NRSE/NRSF regulatory machinery, thereby alleviating transcriptional repression and effecting de-repression. Thus, by virtue of its association with the NRSE, the dsRNA can switch the function of the NRSF/REST trans-acting protein from transcriptional repressor to transcriptional activator. As a consequence, the neuron-specific genes are transcribed resulting in the differentiation of neuronal stem cells into neurons.

As described herein, several of the genes containing the NRSE are essential for establishment and maintenance of the neuronal phenotype; these include neuron-specific cytoskeletal proteins, neurotransmitters and their biosynthetic enzymes, synaptic vesicle components, neurotrophins, and cell adhesion molecules. An NRSE motif is present in the regulatory region of over thirty neuron-specific genes, including for example, synapsin I, sodium channel type II, brain derived neurotrophic factor, Ng-CAM and L1. FIG. 9 provides a table listing further genes that contain the NRSE motif and can be modulated via the invention methods.

Thus, the invention provides a method for modulating gene expression by contacting a cellular system with a double-stranded ribonucleic acid molecule, wherein the double-stranded ribonucleic acid molecule is capable of associating with a regulatory element that controls transcription of one or more genes, and wherein the association results in altered expression of these one or more genes. The nucleic acid molecules and compositions described above are particularly useful in the methods disclosed for mediating gene expression.

In a further embodiment, the invention provides a method for treating a condition associated with reduced expression of one or more genes by administering to a subject an effective amount of a double-stranded ribonucleic acid molecule capable of associating with a regulatory element that controls transcription of the one or more genes. The association between the double-stranded ribonucleic acid molecule and the regulatory element results in increased expression of the one or more genes.

Also provided is a method for controlling a cellular process by modulating the expression of one or more genes involved in cell-type differentiation through administration to a subject of an effective amount of a double-stranded ribonucleic acid molecule capable of associating with a regulatory machinery that controls transcription of the one or more genes involved in cell-type differentiation. In a particular embodiment, the invention is directed to a method for controlling cell-type differentiation by modulating the expression of one or more genes involved in cell-type differentiation through administration to a subject of an effective amount of a double-stranded ribonucleic acid molecule capable of associating with a regulatory machinery that controls transcription of the one or more genes involved in cell-type differentiation.

In a related embodiment provided by the invention cell-type differentiation is modulated in a subject by administering an effective amount of an agent that interferes a function of a double-stranded ribonucleic acid molecule that associats with a regulatory machinery so as to increase the transcription of one or more genes. In this embodiment, an agent can be administered that interferes with the in vivo function of an endogenous dsRNA and prevents the alleviation of transcriptional repression by the dsRNA. For example, for subjects suffering from or predisposed for a condition characterized by hyperproliferation of the nervous system, an agent that interferes with an endogenous NRSE/RE1 dsRNA can prevent the activation of neuron specific genes.

The term "agent" is used herein to denote a chemical compound, a mixture of chemical compounds, a biological macromolecule, or an extract made from biological materials such as bacteria, plants, fungi, or animal (particularly mammalian) cells or tissues. Agents can include ribozymes and other small molecules. Agents are evaluated for potential biological activity by inclusion in screening assays.

Thus, the invention also provides a method of identifying an agent that interferes with an activity of a double-stranded ribonucleic acid molecule that associates with a regulatory machinery of one or more genes by contacting a cellular system comprising the double-stranded ribonucleic acid molecule and the one or more genes with an agent, and identifying an agent that interferes with an activity of said double-stranded ribonucleic acid molecule. An activity of a double-stranded ribonucleic acid molecule actvity can be modulation of gene expression. The interference with an activity of a double-stranded ribonucleic acid molecule can be a result of preventing or reducing the association between the double-stranded ribonucleic acid molecule and the regulatory machinery of one or more genes and can result in modulation of a cellular process, for example, inhibition with cellular differentiation such as neuronal differentiation from stem cells.

The ability to introduce RNA into an intact cell or organism containing a gene that has a corresponding regulatory element, for example, a NRSE, allows applications of the invention in high throughput screening (HTS). For example, an NRSE/RE1 dsRNA can be produced as described herein and added to, for example, a multi-well microtiter plate containing cell samples. Solutions containing dsRNAs that are capable of modulating gene expression can be placed into individual wells positioned on a microtiter plate as an ordered array, and intact cells or organisms in each well can be assayed for any changes or modifications in behavior or development due to modulation of gene expression. An NRSE/RE1 dsRNA also can be fed directly to, injected into, the cell/organism containing the gene or genes whose expression can be modulated by virtue of having an NRSE in tis promoter region. Alternatively, the dsRNA can be produced by in vivo or in vitro transcription from an expression construct. The modulation of gene expression can be assayed from the effects on the cell/organism, for example, a change in differentiative state.

Numerous embodiments for the method described above are included within the scope of the invention. For example, a screening method of the invention can be used to identify an agent that has the ability to interfere with activation of neuron-speficic gene expression by an endogenous NRSE/RE1 dsRNA and therefore can prevent the activation of a neuron specific gene if the agent is added to an appropriate cell line or introduced into a transgenic non-human mammal or into a cell line in which the expression of a target gene is inhibited. Transgenic animals in which the expression of one or more genes is modulated as well as cell lines generated according to this invention can be used in these methods.

Generally a plurality of assay mixtures are run in parallel with different agent concentrations to obtain a differential response to the various concentrations. Typically, one of these concentrations serves as a negative control, i.e. at zero concentration or below the level of detection. Agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of naturally-occurring agents in the form of bacterial, fungal, plant and animal extracts are available or readily produced. Additionally, natural or synthetically produced libraries and compounds are readily modified through conventional chemical, physical and biochemical means, and can be used to produce combinatorial libraries. Known pharmacological agents can be subjected to directed or random chemical modifications, such as acylation, alkylation, esterification, amidification, to produce structural analogs.

The present invention therefore encompasses introduction of dsRNA into a cell for the treatment or prevention of a condition. In particular, the therapeutic applications of the present invention include delivery of the smRNA of the invention into somatic, nonreproductive cells as well as into reproductive, germ line cells of host mammals. Mammals carrying foreign exogenous genes in their germ line, generally referred to as transgenic animals, presently include, for example, mice, rats, rabbits, and some domestic livestock.

A smRNA of the invention can be introduced into a progenitor or stem cell and thereby modulate the expression of one or more genes invovled in cell fate determination, for example, neuronal differentiation. An NRSE/RE1 smRNA of the invention is useful for the treatment of neurological and neurodegenerative disorders. Treatment includes amelioration of any symptom associated with the condition or clinical indication associated with the condition. In particlar, a smRNA of the invention can be administered to a subject having a condition characterized by either a deficiency in the number of neuronal cells or degeneration of neuronal cells.

It is understood that the therapeutic embodiments of the present invention can be practiced with a variety of delivery vector systems known in the art and able to introduce relatively high levels of nucleic acid sequences into a variety of cells. Suitable viral vectors include yet are not limited to Herpes simplex virus vectors (Geller et al., *Science* 241:1667-1669 (1988)); vaccinia virus vectors (Piccini et al., *Meth. Enzymology* 153:545-563 (1987)); cytomegalovirus vectors (Mocarski et al., *Viral Vectors* 78-84 (1988)); Moloney murine leukemia virus vectors (Danos et al., *Proc. Natl. Acad. Sci. USA* 85:6460-6464 (1988); Blaese et al., *Science* 270: 475-479 (1995); Onodera et al., *J. Viol.* 72:1769-1774 (1998)); adenovirus vectors (Berkner, *Biotechniques* 6:616-626 (1988); Cotten et al., *Proc. Natl. Acad. Sci., USA* 89:6094-6098 (1992); Graham et al., *Meth. Mol. Biol.* 7:109-127 (1991); Li et al., *Human Gene Therapy* 4:403-409 (1993); Zabner et al., *Nature Genetics* 6:75-83 (1994)); adeno-associated virus vectors (Goldman et al., *Human Gene*

*Therapy* 10:2261-2268 (1997); Greelish et al., *Nature Med.* 5:439-443 (1999); Wang et al., *Proc. Natl. Acad. Sci., USA* 96:3906-3910 (1999); Snyder et al., *Nature Med.* 5:64-70 (1999); Herzog et al., *Nature Med.* 5:56-63 (1999)); retroviral vectors (Donahue et al., *Nature Med.* 4:181-186 (1998); Shackleford et al., *Proc. Natl. Acad. Sci., USA* 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829.

A viral vector useful for practicing the invention methods, in particular, the therapeutic and prophylactic applications, can be derived from a retrovirus. Retroviridae encompass a large family of RNA viruses that is, in part, characterized by its replicative strategy, which includes as essential steps reverse transcription of the virion RNA into linear double-stranded DNA and the subsequent integration of this DNA into the genome of the cell. A retroviral vector useful in the invention can be a modified lentivirus, for example, an HIV-1, that is used to introduce a nucleic acid sequence into a cell. Lentiviruses are diploid positive-strand RNA viruses of the family Retroviridae that replicate through an integrated DNA intermediate. In particular, upon infection by the RNA virus, the lentiviral genome is reverse-transcribed into DNA by a virally encoded reverse transcriptase that is carried as a protein in each lentivirus. The viral DNA is then integrated pseudo-randomly into the host cell genome of the infecting cell, forming a provirus that is inherited by daughter cells. Known lentiviruses can be readily obtained from depositories or collections such as the American Type Culture Collection ("ATCC"; 10801 University Blvd., Manassas, Va. 20110-2209), or isolated from known sources using commonly available techniques.

Lentiviral vectors based on human immunodeficiency virus (HIV) have been developed that can transduce nondividing cells both in vitro and in vivo. Such vectors are useful in the methods of the invention for administration of a NRSE/RE1 dsRNA to a subject or cellular system because these vectors can stably integrate into the host cell genome to effect long-term expression of the transgene and are free from significant cellular or humoral immune responses demonstrating their utility as delivery vehicles for genes in vivo or in vitro. As the etiological agent of acquired immunodeficiency syndrome (AIDS), safety in the use of lentiviral vectors has been enhanced through a variety of molecular engineering designs that inhibit the generation of replication-competent vectors through fortuitous recombination of vector gene components. Such engineering designs include removal of accessory genes which play a role in virulence, removal of trans-acting factors for transcription, the generation of self-inactivating vectors, separating the packaging signals from the functions required for vector production and splitting the packaging functions into multiple components.

For in vivo gene therapy, cells to be transducted are not removed from the subject. Rather, the dsRNA is introduced into cells of the recipient organism in situ that is, within the recipient. In vivo gene therapy has been reported in several animal models and the methods described herein are specifically contemplated for human gene therapy. For a description of viral vectors and their uses in gene therapy, see, for example, *Gene Therapy: Principles and Applications* (T. Blankenstein, et., 1999, Springer-Verlag, Inc.) and *Understanding Gene Therapy* (N. Lemoine, ed., 2000, R-G Vile), both of which are incorporated herein in their entirety.

Furthermore, in vivo applications encompass transduction of a mammalian cell in utero, more specifically, into the somatic cells of a mid-trimester fetus. In utero gene therapy allows for the correction of some types of genetic diseases before the appearance of any clinical manifestations; in addition, introduction of a therapeutic dsRNA into the fetus offers a number of potential advantages over postnatal gene transfer. For neurologic genetic diseases that appear to produce irreversible damage during gestation, treatment before birth, if desired early in pregnancy, can be useful to allow the birth of a normal baby. If desired, a smRNA of the invention can be incorporated into a gene therapy vector, for example, a lentiviral vector, that can intergrate efficiently into the target cell's genome and therefore insert the therapeutic dsRNA into the genetic make-up of the cell. Successful early treatment with a smRNA of the invention can preempt the appearance of clinical manifestations of a condition by, for example, alleviating the repression of transcription of neuron-specific genes and causing neuronal cell differentiation of neuronal stem cells. Therapeutic intervention with the invention methods is particularly useful during embryonic development since neuronal stem cells still have neuronal differentiation potency that can be exploited by introduction of an NRSE/RE1 dsRNA. Furthermore, gene transfer in the fetus can be more efficient than in the more mature organism, so that gene therapy should be easier to accomplish prenatally than postnatally. In addition, the immunological naivete and the permissive environment of the early gestational fetus allow acceptance of cells and lentivectors without the need for immunosuppression or myeloablation because during early immunologic development, before thymic processing of mature lymphocytes, the fetus is largely tolerant of foreign antigens.

If desired, the smRNA of the invention can be introduced into the cell by administering an vector containing the dsRNA to a mammal that carries the cell. For example, the vector carrying the smRNA of the invention can be administered to a mammal by subcutaneous, intravascular, or intraperitoneal injection. If desired, a slow-release device, such as an implantable pump, can be used to facilitate delivery of the vector to cells of the mammal. A particular cell type within a mammal can be targeted by modulating the amount of the vector of the invention administered to the mammal and by controlling the method of delivery. For example, intravascular administration of a vector to the portal, splenic, or mesenteric veins or to the hepatic artery can be used to facilitate targeting the smRNA of the invention to liver cells. Furthermore, a homing molecule that specifically targets a particular cell type, for example, neuronal precursor cells or stem cell can ne used to target the dsRNA to te dsired target cell. In another method, a vector carrying the smRNA of the invention can be administered to cells or organ of a donor individual (human or non-human) prior to transplantation of the cells or organ to a recipient.

In a preferred method of administration, the vector used to introduce a smRNA of the invention is administered to a tissue or organ containing the targeted cells of the mammal. Such administration can be accomplished by injecting a solution containing the lentiviral vector of the invention into a tissue, such as skin, brain (e.g., the olfactory bulb), kidney, bladder, trachea, liver, spleen, muscle, thyroid, thymus, lung, or colon tissue. Alternatively, or in addition, administration can be accomplished by perfusing an organ with a solution containing the vector used to introduce a smRNA of the invention, according to conventional perfusion protocols.

In another therapeutic embodiment, the vector used to introduce a smRNA of the invention is administered intranasally by applying a solution of the vector to the nasal mucosa of a mammal. This method of administration can be used to facilitate transportation of the vector into the brain. This delivery mode provides a means for delivering the vector used to introduce a smRNA of the invention to brain cells, in particular, mitral and granule neuronal cells of the olfactory bulb, without subjecting the mammal to surgery. In an alternative method, a vector intended to express a dsRNA transgene in the brain can be delivered to the brain by osmotic shock according to conventional methods for inducing osmotic shock.

It is understood that modifications which do not substantially affect the activity of the various embodiments of this invention are also included within the definition of the invention provided herein. Accordingly, the following examples are intended to illustrate but not limit the present invention.

EXAMPLE I

Identification of a Neuron-Specific Small Non-Coding RNA from Adult Hippocampal Neural Stem Cells This example demonstrates that double-stranded NRSE RNA (NRSE dsRNA) exists specifically within the neuronal population and appears at an early stage of neurogenesis.

To investigate the role of small non-coding RNAs in the differentiation of neural stem cells, 20- to 40-nucleotide (nt) RNAs were cloned and sequenced from total RNA extracted from adult hippocampal neural stem cell (HCN-A94) as described by Gage et al., *Proc. Natl. Acad. Sci. USA* 92:11879-83 (1995). (FIG. 1A, left, see Experimental Procedures).

The HCN A94 cells were cultured in DMEM/F12 (Omega Science), supplemented with 2.5 mM L-glutamine (Omega Science) and N2 supplement (N2 medium, Invitrogen) containing FGF-2 (20 ng/ml; recombinant human FGF-2, Papro-Tech) as described by Gage et al., supra, 1995. For neuronal differentiation experiments, cells were cultured in N2 medium containing RA (1 µM, Sigma) and Forskolin (5 µM, Sigma). For astrocyte differentiation, cells were cultured with 50 ng/ml BMP-2 (Sigma), 50 ng/ml LIF (Sigma) and 1% FCS (Hyclone) for 4 to 10 days as described by Nakashima et al., *Science* 284: 479-82 (1999). For oligodendrocyte differentiation, cells were cultured in N2 medium after FGF-2 withdrawal for 2 to 4 days. Cell imaging was performed using an inverted microscope (Nikon TE300) with a SPOT camera.

Briefly, total RNA (about 1 mg) extracted from HCN-A94 cells was loaded on a denaturing 15% PAGE with size marker, EZ-Load molecular ruler (BioRad). 20- to 40-nucleotide (nt) RNAs were separated and recovered. The purified RNA was ligated with 5' phosphorylated nucleotide 3' adapter by T4 RNA ligase (NEB). The complementary primer for the adapter was hybridized and RNA sequences were converted into dsDNA by using Superscript II cDNA cloning kit as following the manufacture's instruction (Gibco-BRL). Annealed 5' end DNA adaptor was ligated with these dsDNA by T4 DNA ligase and amplified by PCR with primers having 5' adapter and 3' adaptor sequences. PCR products were cloned into pCR II plasmid by using the TOPO TA cloning kit (Invitrogen). Cloned sequences were analyzed by Celera mouse gene database (Celera).

Six different neural cell culture samples were used to obtain more than 50 unknown non-coding RNAs. One RNA sequence contained a match to the 21-nt NRSE/RE1 DNA sequence in the antisense orientation ("as NRSE", see FIG. 1A, right). The NRSE/RE1 sequence is usually localized within promoter regions of neuron-specific genes and is recognized by the NRSF/REST protein to restrict neuron-specific gene expression, however the function of a DNA element within an RNA sequence is unclear.

Figures 1B, 1C:
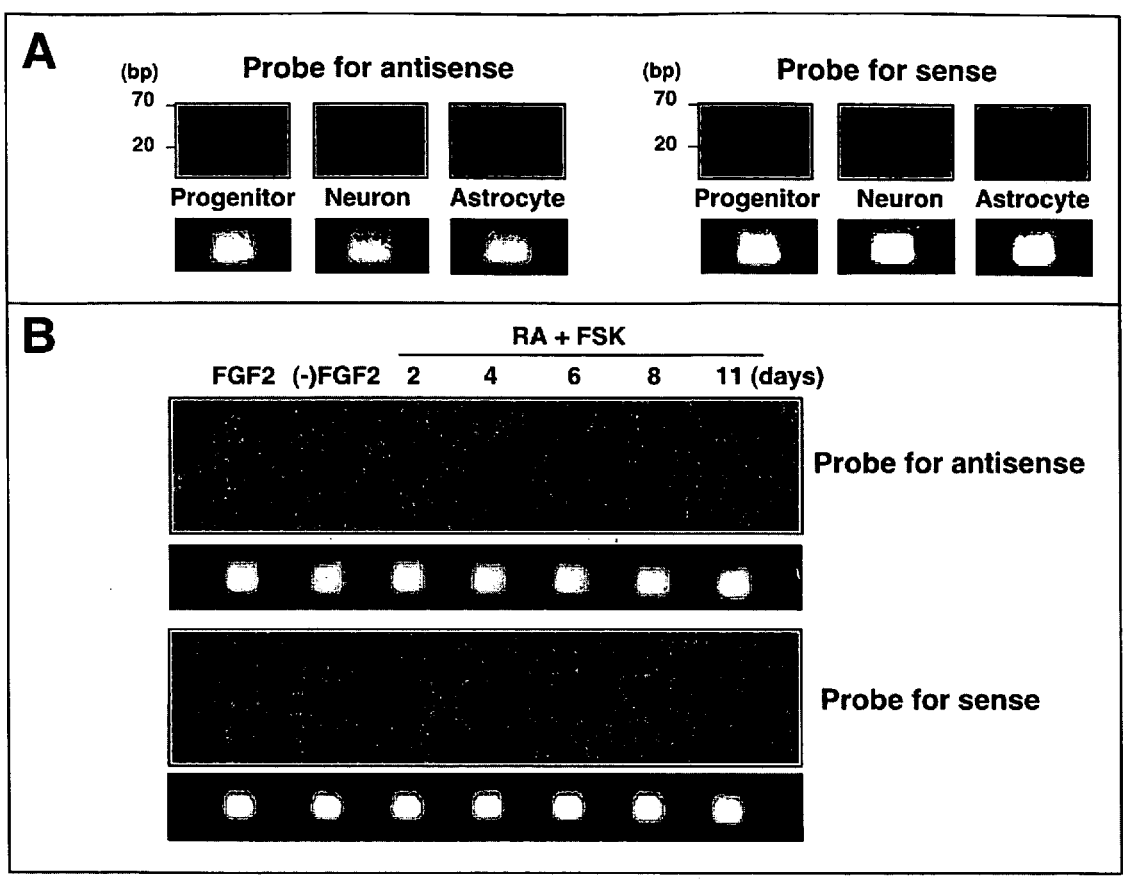
FIG. 1B shows northern blotting analysis of the NRSE dsRNA. Both asNRSE and sNRSE RNA corresponding to approximately 20-nt in length exist in the neuronal population (RA/FSK treated).
FIG. 1C shows time-course Northern blotting analysis after RA/FSK induction. Cells 2- and 4-days after induction of neural differentiation contain highest amounts of the NRSE dsRNA, suggesting that the NRSE dsRNA appears at an early stage of neurogenesis.

Northern Blot analyses of HCN-A94 cells did not identify any transcripts containing asNRSE RNA sequences that were larger than 0.1 kb, but revealed an asNRSE RNA corresponding to about 20-nt in length within the neuronal population (RA+FSK treated), consistent with the data obtained from previous cloning and sequencing experiments (see FIG. 1B, probe for antisense). A control probe for the corresponding sense-strand similarly revealed a ~20-nt sense NRSE RNA ("sNRSE") within the same neuronal population (see FIG. 1B, probe for sense), indicating that these RNAs can exist as a double-stranded form within the cell.

HCN A94 cells were washed twice with PBS and total RNA were extracted and purified with TRIzol reagent (Gibco-BRL). Fifty micrograms of total RNA per lane were loaded on a 3.5% NuSieve-Seakem™ agarose gel (FMC Inc.). After electrophoresis, bands of RNA were transferred to a Hybond-N™ nylon membrane (Amersham Co.). The membrane was probed with synthetic oligonucleotides that were complementary to the sequences of each sNRSE or asNRSE. A synthetic probe complementary to the sequence of each respective RNA was used, and all probes were labeled with $^{32}P$ by T4 polynucleotide kinase (NEB). Pre-hybridization and hybridization were carried out using EazyHyb solution (Clontech) following manufacturer instructions. The membrane was rinsed in 2×SSC twice at room temperature for 20 minutes.

Low amounts of both sense and antisense RNAs could also be detected within the progenitor population, but the expression levels in the neuronal population was much higher relative to the progenitor population. The expression of low levels of sense and antisense RNAs within the progenitor cultures is due to the presence of cells already committed to specific lineages. Consistent with this observation, no RNAs were detected within an astrocyte population, confirming that double-stranded NRSE RNA (NRSE dsRNA) exists specifically within the neuronal population.

To determine which neuronal stages express the NRSE dsRNA, a time-course Northern blotting analysis was performed after neuronal induction. Cells 2- and 4-days after induction of neural differentiation (RA+FSK) contained highest amounts of the NRSE dsRNA; as maturation proceeded, the levels of the NRSE dsRNA apparently decreased (FIG. 1C). These data show that the NRSE dsRNA appeared at an early stage of neurogenesis, rather than at more mature stages.

EXAMPLE II

Neuronal Lineage Induction by the NRSE dsRNA

This example shows that the NRSE dsRNA induce progenitor cells to become neurons and is alone sufficient to trigger differentiation.

The small non-coding NRSE dsRNA were expressed in HCN-A94 neural stem cells to determine their function. Briefly, lentiviral vectors with U6 promoter driven-sNRSE, -asNRSE and -NRSE dsRNA expression cassettes were prepared as follows. The sNRSE RNA- and asNRSE-expression lentiviral vectors were constructed by using CSC PW, a lentiviral vector that contains the CMV promoter as descibed by Miyoshi et al., *J. Virol.* 72:8150-8157 (1998); and Pfeifer et al., *Proc. Natl. Acad. Sci. USA* 98:11450-5 (2001), both of which are incorporated herein by reference in their entirety.

The CMV promoter was digested out by XbaI and ClaI, and substituted with pol III murine U6 promoter (CS U6 PW; at +1 G residue of transcription start site of U6 promoter, the terminator sequence UUUUU was inserted directly. The CS U6 PW derived lentivirus was used as control mock virus in each experiment). U6 driven each NRSE RNA sequence with the terminator sequence at the 3' end was first amplified by PCR with primers containing ClaI and HpaI, and cloned by TOPO TA cloning kit (Invitrogen). Each U6 cassette was sub-cloned into CSC PW by using ClaI and PmeI sites. Ribozyme expression lentiviral vectors were constructed similarly. The dsNRSE RNA-expression lentiviral vectors was constructed by linking two U6 cassettes for sNRSE RNA and asNRSE as "face to face" orientation [two U6 terminators were ligated with multicloning site (MCS) sequeunce of pBlueScript SK].

The production of lentivirus was performed according to the procedures described by Naldini et al., Science 272: 263-7 (1996); and Pfeifer et al., supra, 2001, both of which are incorporated herein by reference in their entirety.

Murine 6 kb Sox2 promoter sequence on Sox2 pBS SK plasmid was inserted into pNeoLuci plasmid at the site of MCS sequence, where the d2EGFP gene on pd2EGFP plasmid (Clontech) was substituted with the luciferase gene. Murine 6 kb □III-tubulin promoter, 8 kb GFAP promoter and 4.5 kb MBP promoter were PCR-subcloned by using mouse genomic DNA, the sequence of which was assessed from Celera mouse gene database, and each promoter was inserted into pNeoLuci plasmid upstream of the luciferase gene. Rat 2 kb GluR2 promoter was also PCR-subcloned by using rat genomic DNA, and the promoter was inserted into pd2EGFP plasmid (Clontech). The TATA, NRSE-TATA and mtNRSE-TATA luciferase reporter plasmids were constructed by using the pGL2-basic plasmid (Promega). About 260-bp minimal CMV promoter DNA was amplified with 5' primer containing NRSE or mtNRSE sequence cloned into pCR II plasmid by TOPO TA cloning kit (Invitrogen). Each KpnI and BamHI digested fragment was sub-cloned into KpnI and BglII sites on the pGL-basic plasmid.

Figure 2A:
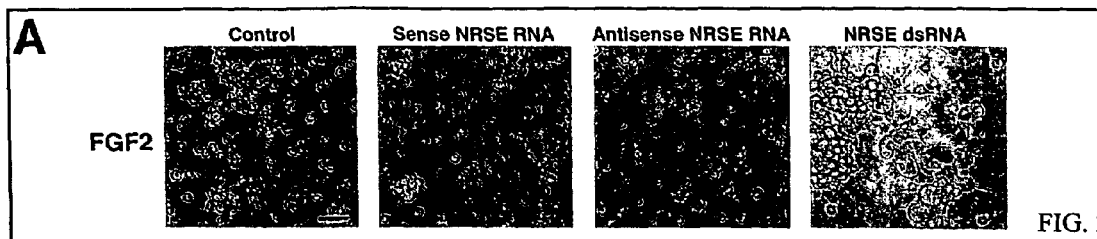
In FIG. 2A, the NRSE dsRNA was expressed in HCN-A94 neural progenitor cells with either a control virus or viruses expressing sense, antisense or dsNRSE RNAs.

After infecting progenitor cells with virus, the cells were maintained under conditions with or without 20 ng/ml FGF-2, in the event that cells behave differently in the presence of mitogen. Infections were almost 100% (viral titers were >1.5×10$^4$ Tu/ng defined by the P24 assay). In control infections (lentivirus with an empty U6 cassette), no obvious effects either on cell morphology or behavior were observed (see FIG. 2A). Expression of single sense-strand or antisense-strand NRSE RNA alone also had no obvious effects on cell morphology (see FIG. 2A). However, upon co-introduction of sense and antisense strands of NRSE RNA significant morphological changes were observed (FIG. 2A). In particular, the cells extended processes indicative of differentiation and some of the cells made large but flat clusters with long processes. Some cell death was observed in the NRSE dsRNA-treated cultures grown in the presence of FGF-2, but the apparent toxicity was considerably reduced the progenitor cultures were treated with the NRSE dsRNA in the absence of FGF-2.

Since the expression of NRSE dsRNA in HCN-A94 cells mediated some aspects of differentiation, immunocytochemistry was subsequently performed with markers of various differentiated neural lineages.

Briefly, cells were washed in fresh PBS and fixed in fix/permeablization buffer (50 mM HEPES/KOH, pH 7.5, 50 mM potassium acetate, 8 mM MgCl$_2$, 2 mM EGTA, 2% paraformaldehyde, 0.1% NP-40, 0.02% SDS) for 15 minutes at room temperature. Cells were rinsed three times in PBS for 10 min. Seventy micrograms of FITC-labeled oligodeoxynucleotide probe with a sequence complementary to asNRSE and 20 µg of tRNA from E. coli MRE 600 (Boehringer Mannheim, Mannheim, Germany), dissolved in 10 µL of deionized formamide, were denatured by heating for 10 minutes at 70° C. The mixture was then chilled immediately on ice. Ten microliters of hybridization buffer, containing 20% dextran sulfate and 2% BSA in 4×SSC, were added to the solution of the denatured probe. Twenty microliters of hybridization solution containing the probe were placed on the cells and incubated for 16 h at 37° C. Cells were rinsed in 2×SSC/50% formamide and in 2×SSC at room temperature for 20 minutes each. The coverslip was mounted with Vectashield (Vector Laboratories, Burlingame, Calif.).

Immunofluorescence studies were performed basically as described by Gage et al., supra, 1995, using rabbit anti-beta tubulin-III (TUJ1; 1/7500, Covance), guinea pig anti-GFAP (1:500; Advanced Immunochemical, Inc), rabbit anti-NF200 (Advanced Immunochemical, Inc), mouse anti-RIP (1/250, Immuno), rabbit anti-Calbindin (Advanced Immunochemical, Inc) and DAPI (4',6-diamidino-2-phenylindole, Sigma). All secondary antibodies were from Jackson. Double labeling was analyzed using a Bio-Rad Radiance confocal imaging system (Hercules, Calif.).

Figure 2B:
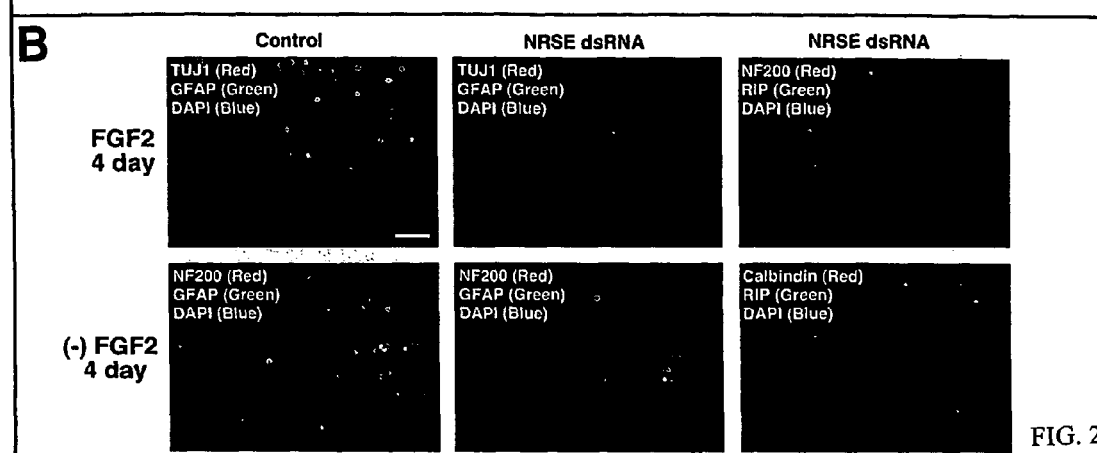
FIG. 2B shows immunocytochemical analysis of cells with the NRSE dsRNA.

As shown in FIG. 2B, introduction of NRSE dsRNA in progenitor cultures resulted in increased immunocytochemical staining of neuron-specific markers including □III-tubulin (TUJ1), NF200 and calbindin. The cells also appeared to have neuronal-like morphology, as evidenced by the extension of processes. Cells containing the NRSE dsRNA were completely negative for the astrocyte marker GFAP and oligodendrocyte marker RIP (FIG. 2B).

These results suggest that the NRSE dsRNA can function as a neuron-specific inducer. Furthermore, the observation that the introduction of NRSE dsRNAs (without mitogen) can induce progenitor cells to become neurons suggests that NRSE dsRNAs alone are sufficient to trigger differentiation.

EXAMPLE III

Quantitative Analysis of NRSE dsRNA Activity as an Endogenous Inducer of Neuronal Differentiation This example shows that the NRSE dsRNA acts as a specific endogenous neuronal inducer by up-regulating genes important for neuronal differentiation.

In order to assess the effects of non-coding NRSE dsRNA during lineage-specific differentiation, stage-specific promoter-based reporter assays were used to quantify the activity of NRSE dsRNAs comparatively. The specificity of each promoter was confirmed at the beginning of each experiment.

A Sox2 promoter-driven luciferase construct was used as a neural stem cell-specific reporter construct. Luciferase values from cells 4 days after mock virus (control) infection was set as 100% (FIG. 2C, the immunostaining is also shown in right panel). Luciferase activity was measured with Dual-Luciferase™ Reporter Assay System (Promega) according to the manufacturer's protocol. Cells were lysed in 150 µl of 1× reporter lysis buffer for 15 min and scraped off the plate. The cell debris was removed by centrifugation. After adding 20 µl of lysate to 100 µl of Luciferase Assay Reagent II, the luminescent signal was immediately quantitated with a luminometer (Lumant LB 9501).

No obvious difference was observed for sNRSE RNA and asNRSE RNA. However, as indicated in FIG. 2B, a significant decrease in Sox2 luciferase activity was observed in cells infected with NRSE dsRNA, due to these cells becoming neurons.

A βIII-tubulin (TUJ1) promoter-driven luciferase construct was used for the neuron-specific reporter construct. Each RNA expressing virus infected HCN-A94 progenitor cells was cultured in 1 μM RA and 5 μM FSK for 4 days (neuron-promoting condition). The βIII-tubulin promoter-driven luciferase activity increased more than 4 times when compared with the activity in the progenitor culture (data not shown). Many cells stained positive for βIII-tubulin (control with mock virus infection, FIG. 2C) thus the luciferase value of the cell at this time point was taken as 100%. Expression of either sNRSE RNA or asNRSE RNA alone had no obvious effects on neuronal differentiation, similar to the results of Sox2-luciferase assay. In contrast, the NRSE dsRNA specifically increased the βIII-tubulin promoter-driven luciferase activity more than 2 times relative to control.

Figure 2C:
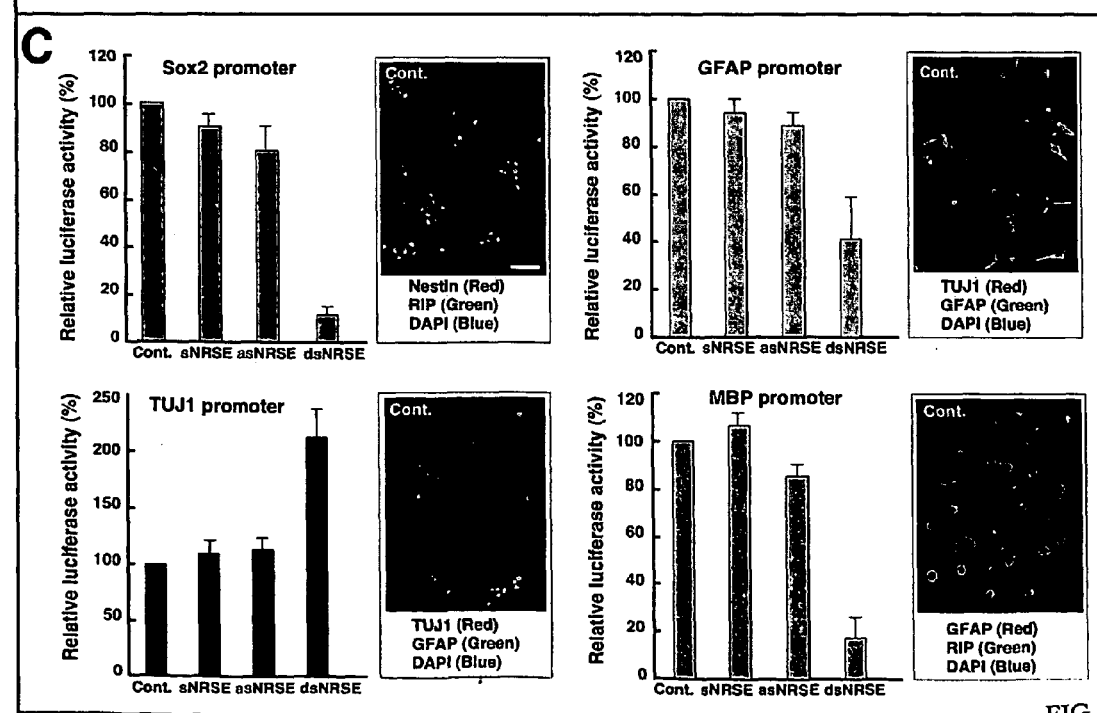
FIG. 2C shows quantitative analysis of the NRSE dsRNA activity as an inducer of neuronal differentiation. The reporter assay was performed by using lineage-specific gene promoter-driven luciferase constructs. The results shown are the averages of results from three sets of experiments.

The GFAP promoter and MBP promoter were prepared as lineage-specific luciferase assays, for astrocyte and the oligodendrocyte differentiation, respectively. To induce astrocyte differentiation, cells were treated with a combination of 50 ng/ml BMP-2, 50 ng/ml LIF and 1% FCS. Four days later, the GFAP promoter-driven luciferase activity increased more than 5-fold when compared with the activity in the progenitor culture as shown by the immunostaining in FIG. 2C. As for oligodendrocyte differentiation, FGF2 withdrawal of progenitor cultures resulted in some spontaneous differentiation. Two days later, the MBP promoter-driven luciferase activity increased more than 3-fold when compared with the activity in progenitor cultures (FIG. 2C).

No obvious differences were detected in the cases where sNRSE RNA and asNRSE RNA were expressed during astrocyte or oligodendrocyte differentiation compared to control. However, significant decreases in luciferase activity were detected when the NRSE dsRNA was introduced at progenitor stages under each differentiation process. Furthermore, the NRSE dsRNA-treated cells that remained under each differentiation condition appeared to be neurons as measured by βIII-tubulin staining.

The above results show that the NRSE dsRNA is acting as a specific endogenous neuronal inducer by up-regulating genes important for neuronal differentiation.

EXAMPLE IV

Increased Expression of Neuron-Specific Genes Containing NRSE/RE1 by the NRSE dsRNA This example shows that the NRSE dsRNA mediates its activity directly on NRSE-containing genes and not through regulating the expression of the NRSF/REST protein itself. The example further demonstrates that the NRSE dsRNA activates, rather than silences, the transcription of NRSE/RE1-containing genes and that this transcriptional activation is mediated through the promoter region containing the NRSE/RE1 sequence.

As shown in FIG. 2, the neuronal lineage induction is one of the major effects of the NRSE dsRNA in progenitor cultures. If the NRSE dsRNA mediated the silencing of the NRSF/REST gene itself by a mRNA/siRNA-like function and NRSF/REST functions as a repressor of neuronal gene expression, the repression of neuron-specific genes would be eliminated resulting in neuronal lineage induction. However, there is no apparent NRSE sequence within the NRSF/REST mRNA, therefore making it an unlikely target at the post-transcriptional level by the NRSE dsRNA.

Figures 3A, 3B, 3C, 3D:
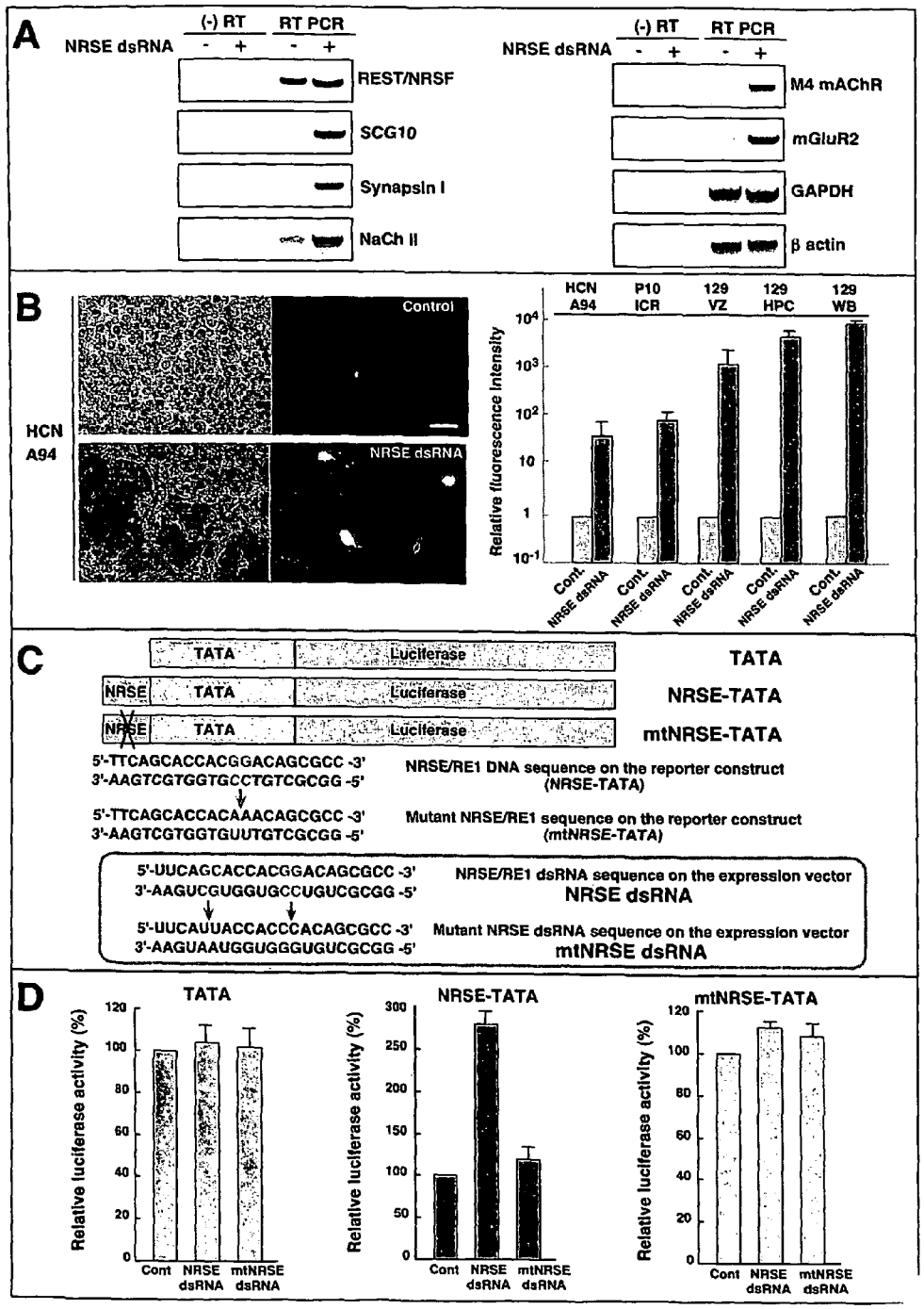
FIG. 3A shows RT-PCR analysis demonstrating that the NRSE dsRNA increased transcription levels of NRSE/RE1-containing genes (SCG10, Synapsin I NaCh II, M4 mAChR and mGluR2) without affecting the expression of NRSF/REST.
FIG. 3B shows a reporter assay for the NRSE dsRNA activity using the mGluR2 promoter-driven EGFP construct. Relative fluorescence intensity is shown plotted on a Log scale (right)
FIG. 3C shows a schematic diagram of the constructs to examine the requirement of sequence specificity of NRSE. The NRSE/RE1 element was fused upstream of TATA box and linked to the luciferase gene.
FIG. 3D shows the sequence requirement of both the NRSE dsRNA and NRSE/RE1 DNA element for the gene activation.

To confirm that the regulation does not take place at a post-transcriptional level, total RNAs were extracted from HCN-A94 progenitor cultures treated with and without NRSE dsRNA. As shown in FIG. 3A, reverse transcription PCR analysis revealed that the introduction of the NRSE dsRNA did not appear to change the expression of the NRSF/REST itself (FIG. 3A, top left).

To determine the direct effects of the NRSE dsRNA, the effect on the expression of neuron-specific genes that have the NRSE/RE1 DNA element in their promoter regions was assessed, in particular, SCG10, Synapsin I NaCh II, M4 mAChR and mGluR2. In parallel with NRSE/RE1-containing gene products, the expression levels of GAPDH and β-actin were assessed as controls. RT-PCR analysis revealed that the NRSE dsRNA increased transcription levels of NRSE/RE1-containing genes (FIG. 3A). In the progenitor stages, endogenous expression levels of neuron-specific genes with NRSE/RE1 element, SCG10, Synapsin I NaCh II, M4 mAChR and mGluR2, were very low. Upon introduction of NRSE dsRNA, significant transcriptional activation was observed (FIG. 3A). These gene activating events appeared to be NRSE/RE1-gene specific as no obvious increases in the expression of GAPDH and β-actin genes were detected.

The above results suggest that the NRSE dsRNA does not function as an mRNA/siRNAs, and can instead mediate the specific transcriptional activation of neuronal genes containing NRSE/RE1 elements.

To determine how widespread the NRSE dsRNA-dependent gene activation was, the NRSE dsRNA activity was detected with a reporter assay using the mGluR2 promoter. To this end, the mGluR2 promoter containing an NRSE/RE1 DNA element was fused to EGFP and introduced the construct into various cell types with or without the NRSE dsRNA. In HCN-A94 progenitor cultures without the NRSE dsRNA, most of the cells were negative for GFP expression (FIG. 3B). In contrast, in progenitor cultures with the NRSE dsRNA, the number of GFP positive cells dramatically increased and the expression levels of GFP within a cell also increased (FIG. 3B).

Furthermore, neurosphere cultures were prepared from whole brain of 10-day old ICR strain mice, and primary neural stem cells were derived from ventricular zone, hippocampus and whole brain of 129 strain adult mice. In all cases, the introduction of NRSE dsRNA mediated a substantial increase in mGluR2 promoter activity.

Taken together, these results show that NRSE dsRNA mediates its activity directly on NRSE-containing genes and not through regulating the expression of the NRSF/REST protein itself. The results also demonstrate that the NRSE dsRNA activates rather than silences the transcription of NRSE/RE1-containing genes and that the transcriptional activation is mediated through the promoter region containing NRSE/RE1 sequence; the EGFP mRNA does not contain any NRSE sequences as a target for the NRSE dsRNA so that an mRNA/siRNA-like effect is unlikely. Furthermore, the above results show that the NRSE dsRNA effects on gene activation represent a general mechanism for a broad class of neural stem cells for the regulation of neuronal genes and is not restricted to hippocampal stem cells.

EXAMPLE V

Critical Sequence Requirement of Both the NRSE dsRNA and NRSE/RE1 DNA Element for Gene Activation This example shows that the NRSE dsRNA-dependent gene activation requires a critical sequence homology between the NRSE/RE1 DNA element and the NRSE dsRNA.

To investigate the sequence requirement and specificity, a simple reporter assay system was constructed with the NRSE/

RE1 element fused upstream from the ubiquitous 260-bp CMV minimal promoter carrying a TATA box and linked to the luciferase gene (NRSE-TATA, FIG. 3C). A mutated NRSE/RE1 element at a key recognition site was similarly prepared (mtNRSE-TATA, FIG. 3C, the mutated sequence is shown in the middle). We also made expression cassettes for the NRSE dsRNA and a mutated NRSE dsRNA (mtNRSE dsRNA, FIG. 3C). Notably, the luciferase gene does not contain any NRSE elements.

When the TATA-luciferase constructs lacking the NRSE/RE1 element were introduced into HCN-A94 cells, no differences in the luciferase activities were detected between cells expressing no RNA (control), NRSE dsRNA and mtNRSE dsRNA (FIG. 3D, Grey bars). In contrast, when NRSE-TATA-luciferase constructs were introduced, the NRSE dsRNA increased the expression levels of NRSE-TATA-luciferase gene (FIG. 3D, Orange bars). The amount of increase by the NRSE dsRNA was more than 2.5 times in HCN-A94 cells relative to the control. In addition a two-fold increase in 293T cells and a five-fold increase in PC12 cells was also observed.

Subsequently, the effect of a mutated NRSE dsRNA on NRSE-TATA-luciferase activity was assessed. The mutations change sequence specificity, while still preserving double-stranded RNA structure. Interestingly, when the NRSE dsRNA was mutated (mtNRSE dsRNA), no additional increase relative to control was observed (FIG. 3D). On the other hand, the introduction of a mutated NRSE/RE1 DNA element (mtNRSE-TATA) in combination with an intact NRSE dsRNA was not enough for further gene activation (FIG. 3D, Green bars). Similar results were seen in 293T cells and PC12 neuroblastoma cells.

These results show that the NRSE dsRNA-dependent gene activation requires a critical sequence homology between the NRSE/RE1 DNA element and the NRSE dsRNA.

EXAMPLE VI

RNA-Directed Chromatin Changes of NRSE/RE1 Containing Genes in Adult Hippocampus Neural Cells This example shows that, upon introduction of NRSE dsRNA into stem/progenitor cells, the repressor proteins MeCP2, MBD1 and HDAC1 are no longer associated with the NRSE/RE1, resulting in the activation of neuronal genes responsible for neuronal differentiation.

To investigate the nature of the transcription activation of neuron-specific NRSE/RE1-containing genes by the NRSE dsRNA, chromatin immunoprecipitation (ChIP) assays were performed. The promoter regions of mGluR2 and SCG10 genes were assessed as representative NRSE/RE 1-containing neuron-specific genes, since these genes have been characterized in mechanistic studies of the NRSF/REST repressor complex (as described by Brene et al., *Eur J Neurosci* 12:1525-33 (2000); Chen et al., *Nat. Genet* 20:136-142 (1998); Huang et al., *Nat. Neurosci* 2:867-72 (1999); Kim, *Mol Cells* 8:600-5(1998); Lunyak et al., *Science* 298:1747-1752 (2002); Mori et al., *Neurobiol Aging* 23:255-62 (2002); Myers et al., *J Neurosci* 18:6723-39 (1998); Naruse et al., *Proc. Natl. Acad. Sci. USA* 96:13691-6 (1999); Palm et al., *J Neurosci* 18:1280-96 (1998); Schoenherr et al., *Current Opinions in Neurobiology* 5:566-71 (1995b); Schoenherr et al., *Proc. Natl. Acad. Sci. USA* 93:9881-9886 (1996)).

ChIP samples were prepared from HCN-A94 cells at stem/progenitor (FGF2 condition) and differentiated stages (neurons, astrocytes, and oligodendrocytes) and assayed for the association of the mGluR2 and SCG10 genes with various components of the NRSF/REST complex (FIG. 4A).

At stem/progenitor stages, as well as non-neural stages (oligodendrocytes and astrocytes), both mGluR2 and SCG10 genes were associated with NRSF/REST and HDAC 1 (FIG. 4A, second and third columns). Notably, NRSF/REST was always found to be associated with endogenous mGluR2 and SCG10 promoters, in the region of the NRSE/RE1 (FIG. 4A, second columns). In the case of mGluR2 promoter DNA, in addition to HDAC1, methyl-DNA binding proteins of MeCP2 and MBD1 were also found associated with the NRSE/RE1 region. As for the SCG10 promoter, a decreased association of MeCP2 and MBD1 was observed even though this gene is apparently repressed in the non-neuronal state, suggesting diversity of the repression machinery depending on specific gene/promoters containing NRSE/RE1 elements.

In contrast, evidence of de-repressed chromatin states was evident for both mGluR2 and SCG10 genes in neurons, where HDAC1 was no longer found to be associated with NRSE/RE1 element. Moreover, there was increased acetylated histone H4 and acetylated histone H3 with both promoter DNAs, suggesting that active expression could be triggered in adult hippocampus neural cells (FIG. 4A, sixth and seventh columns, third lanes). SWI/SNF chromatin remodeling factors, BRG1 and BAF170, were also found to associate with the NRSE/RE1 element, as part of a possible machinery to remodel the chromatin state for active expression of neuron-specific genes in neuronal cells (FIG. 4A, eighth and ninth columns).

Importantly, the ChIP assay revealed that, upon the introduction of NRSE dsRNA into stem/progenitor cells, the repressor proteins MeCP2, MBD1 and HDAC1 were no longer associated with the NRSE/RE1, resulting in the activation of neuronal genes responsible for neuronal differentiation. The fact that NRSF/REST still occupied the NRSE/RE1 locus indicates that NRSF/REST can be involved in an alternative chromatin structure with acetylated histones to activate transcription. It is likely that for this transition step to occur, chromatin remodeling factors like BAF170 and BRG1, that had previously been shown to bind NRSF/REST (as described by Battaglioli et al., *J. Biol. Chem.* 277:41038-41045 (2002)), are required for remodeling the chromatin by their ATPase activity.

EXAMPLE VII

Diversity of Regulatory Repression Patterns of Neuron Specific Genes with the NRSE/RE1-Containing Neuron-Specific Sequences This example shows differences in repression responses among neuronal genes, indicating the existence of diversity among the REST/NRSF regulatory machinery.

HCN A94 cells were treated with either an HDAC inhibitor trichostatin A (TSA) or with de-methylation reagent 5'-azacytidine (5AzaC). Total RNAs was extracted from the cell that had been treated with 5 nM TSA for 2 days and 3 µM 5AzaC for 4 days. RNA samples were also prepared from the HCN A94 cells infected with lentivirus to express either NRSE dsRNA or mtNRSE dsRNA (RNA was extracted 4 days after the infection). By using these RNAs, RT PCR analysis was performed with specific genes (mGluR2, NaCh II, SCG10, Synapsin I and M4 AchR), and a control gene which lacks NRSE/RE1 sequences (GAPDH).

Compared with the level of control mRNA in untreated HCN A94 progenitor cultures (FIG. 4C), endogenous expression levels of mRNAs of mGluR2, NaCh II, SCG10 and Synapsin I were increased in TSA-treated cells with no effects on the expression on GAPDH (FIG. 4B). The level of M4 AChR mRNA was slightly higher than that of the TSA-treated controls. However, the treatment with 5AzaC showed significant activation of the M4 AChR gene. Similarly, treatment with 5AzaC dramatically increased the expression of mGluR2 and NaCh II mRNAs.

These differences in repression responses among neuronal genes indicate that diversity exists among the REST/NRSF regulatory machinery. Such differences in the repression can be reflected in the detailed specificity of expression timing, tissue and age dependency, maturation and/or each selective subtype of neurons, even though the diversity is generated by a common elemental-directed regulator (NRSE/NRSF).

EXAMPLE VIII

NRSF/REST is Converted from a Trancriptional Repressor to an Activator in the Presence of NRSE dsRNA This example demonstrates that transactivation of genes by NRSE dsRNA is caused by a functional switch of NRSF/REST from repressor to activator.

GluR2 promoter-driven luciferase constructs [wild-type (GluR2-luciferase, FIG. 4C) were prepared and mutated by substituting the NRSE with random nucleotides (mtGluR2-luciferase, FIG. 4C)]. The level of luciferase activity was compared with and without expression of NRSE dsRNA in adult neural stem cells (FIG. 4C). NRSF/REST cannot bind to mutated NRSE sequences (Kraner et al., Neuron 9:37-44 (1992)).

In the case of the mutated NRSE construct (mtGluR2-luciferase), the relative luciferase activity is seen at baseline levels, presumably due to a release of NRSF-mediated repression (derepression). A two-fold increase in the wild-type GluR2-luciferase construct takes place upon introduction of the NRSE dsRNA, but not the mtGluR2-Luciferase construct, demonstrating an activation effect. This activation was never observed with the introduction of a mutant NRSE dsRNA or a control vector; in fact there was an active repression of GluR2-luciferase, consistent with NRSF/REST actions as a repressor.

Taken together, these results indicate that 1) NRSF/REST functions as a repressor in the absence of NRSE dsRNA, 2) NRSF/REST converts to an activator in the presence of NRSE dsRNA, and 3) the activator function of NRSF/REST is dependent on having both a wild type NRSE/RE1 DNA sequence and a wild type NRSE dsRNA.

EXAMPLE IX

Loss of NRSE dsRNA Blocks Neuronal Differentiation in Adult Hippocampus Stem Cells This example shows that NRSE dsRNAs are required for neuronal differentiation and neuron-specific gene expression in adult multipotent stem cells.

To determine if the NRSE dsRNA is necessary for neuronal differentiation of adult hippocampal stem cells, a specific ribozyme (Rz) was designed that can specifically cleave one of the strand of the dsRNA sequence, thus inactivating the expression of the NRSE dsRNA. Ribozymes are RNA-based enzymes, and among the various ribozymes, hammerhead ribozymes have been used as efficient gene knock-down tools to investigate gene function (Eckstein et al., *Catalytic RNA in nucleic acids and molecular biology*, Berlin, Germany, Springer-Verlag (1996); Kuwabara et al., *Mo Cell* 2:617-27 (1998); Scanlon, *Therapeutic Applications of Ribozymes* (Totowa, N.J., Humana Press) (1998); Tanabe et al., *Nature* 406: 473-4 (2000); Turner, *Ribozyme Protocols* Vol. 74 (1997)). Currently, RNAi has been frequently used as a powerful gene knock-down tools (Bernstein et al., *Nature* 409:363-366 (2001); Elbashir et al., *Nature* 411:494-8 (2001); Fire et al., *Trends Genet* 15:358-63 (1998); Miyagishi et al., *Nat Biotechnol* 20:497-500 (2002); Sharp, *Genes Dev* 15:485-90 (2001); Zamore, *Nat Struct Bio* 8:746-50 (2001)). RNAi works in cells through the sequence homology based recognition similar to ribozymes, and could induce gene silencing by the addition of intracellular protein complex on its basic catalytic machinery. In the case of ribozyme, additional proteins are not needed for catalysis (only requires divalent metal ion such as $Mg^{2+}$ ions which are abundant in cells), simply ribozymes can cleave RNA strands in situ (as described by Takagi et al., *Nucleic Acids Res* 29:1815-34 (2001); Warashina et al., *Curr. Opin. Biotechnol.* 11:354-362 (2000)). Since it is important to select the appropriate promoter to express the ribozyme in the compartment of the cell where the target RNA is located (as described by Koseki et al., *J Virol.* 73:1868-1877 (1998)), we first analyzed the localization of NRSE dsRNA by Northern Blotting. We found both antisense and sense NRSE RNAs dominantly expressed in the nuclear fraction (FIG. 5A), reinforcing the finding that NRSE dsRNAs are not acting as miRNAs, which target cytoplasmic mRNAs to inhibit their translation. Treatment of progenitor cells with the ribozyme completely abolished expression of the NRSE dsRN. An inactive ribozyme (I-Rz) with one nucleic acid substitution in the catalytic domain was prepared as a negative control and did not affect NRSE dsRNA expression.

Both nuclear specific U6-driven functional Rz and inactive ribozyme (I-Rz) were introduced into HCN A94 cells by lentivirus infection. No obvious effects were detected at the progenitor stage compared with the cell in which the NRSE dsRNA had been introduced by lentivirus (FIG. 5B). When the culture was switched into the neuronal differentiation condition (RA+FSK), in the case of I-Rz, normal neuronal differentiation was observed (FIG. 5B, bottom right). However, when the Rz targeting NRSE dsRNAs was introduced, neural stem cells displayed strong anti-differentiation effects even with RA and FSK stimulation and resembled the morphology of cells in progenitor stages (FIG. 5B, top right).

In order to determine the effect of Rz in each differentiation pathway, a cell type-specific promoter-based reporter assay was performed similar to that shown in FIG. 2C. Luciferase values from cells 4 days after control mock virus-infection were taken as 100%.

Under progenitor culture conditions, Sox2 promoter-driven luciferase values resulted in no difference in the cases of Rz and I-Rz treatment, probably due to lack of endogenous dsRNA (FIG. 5C).

Under the neuronal condition, the level of the NRSE dsRNA increased, as well as βIII-tubulin (TUJ1) promoter-driven luciferase activity. Introduction of the Rz in this condition reduced the TUJ1 promoter-driven luciferase activity significantly, while the I-Rz had no effect (FIG. 5C). Mutant NRSE dsRNA (mtNRSE dsRNA) had no effect on various luciferase assays.

Under astrocyte or oligodendrocyte differentiation conditions, no obvious differences were detected in the levels of luciferase driven from the GFAP or MBP promoter respectively, upon either Rz or I-Rz introduction (FIG. 5C).

These results show that NRSE dsRNAs are required for neuronal differentiation and neuron-specific gene expression in adult multipotent stem cells. Furthermore, as exemplified herein introduction of a ribozyme targeted against the NRSE dsRNA has anti-neuronal differentiation effects, suggesting that NRSE dsRNAs are also necessary to induce neuronal differentiation.

EXAMPLE X

Localization of the NRSE dsRNA in the Nuclei of Cells Differentiating into Neurons To assess the NRSE dsRNA localization, in situ hybridization against NRSE dsRNA and immunostaining for NRSF/REST protein were carried out simultaneously.

As illustrated in FIG. 6A, DAPI (blue) and NRSE RNA (green) co-localized in the nucleus of HCN-A94 cells in neurons (RA+FSK for four days, upper panels). However, co-localization did not occur when DNA was condensed during cell division (White arrow in FIG. 6A, upper panel). During DNA condensation, NRSE RNAs remained in the nuclear domain but appeared to be outside of the condensed chromosomal region (White arrows, FIG. 6A, upper panel). NRSE dsRNA localization in mitotic cells seems to reflect the localization of histone acetylase/proteins, which also appear beyond the condensed chromosomal region. The nature of their actions on transcriptional regulation is in accord with the finding that transcription is repressed during mitosis (as described by Kruhlak et al., *J. Biol. Chem* 276:38307-38319 (2001)). Molecules less than about 50~70 kDa can translocate back and forth through the nuclear pore through a process of natural diffusion (as described by Stehno-Bittel et al., *Science* 270:1835-1838 (1995)). Since NRSE dsRNAs are approximately 20 bp in length they can diffuse throughout the cell. However, the NRSE dsRNA were located only in nucleus, indicating that an as yet unknown molecule(s) restricts the localization of the dsRNA in nucleus.

NRSF/REST proteins are mainly localized in the nucleus, regardless of cell division (magenta, FIG. 6A, lower panel, left). Even though NRSF/REST is expressed in all cells, the cells expressing higher levels of NRSE RNA were also ☐III-tubulin (Yellow) positive (Red arrows in FIG. 6A). Conversely, cells that expressed the NRSE RNA at the lowest levels corresponded to beta tubulin III (TujI) negative cells (Blue arrows in FIG. 6A).

These results demonstrate that NRSE dsRNAs are localized in cell nuclei, and are concentrated within chromosomal regions. The results further demonstrate that NRSE dsRNAs levels are high in cells that are active in neurogenesis (TUJ1 positive. In addition, the above-described results show that NRSF/REST are expressed in both TUJ1 positive and negative cells and that NRSF/REST or other proteins sequester NRSE RNAs to the nucleus.

EXAMPLE XI

Association Between NRSF/REST and the NRSE dsRNA

In order to examine the potential associations between NRSF/REST and the NRSE dsRNA, an extract of HCN A94 cells was incubated with the biotin-labeled NRSE dsRNA. Biotin-labeled NRSE dsDNA was prepared as a positive control. To assess the specificity in the association, biotin-labeled dsRNA and dsDNA were used as negative controls with the partial sequence of the multi-cloning site (MCS) in pBlue-Script II SK+. Proteins that had bound to the biotin-labeled oligos were "pulled down" with streptavidin beads and were analyzed by Western blot analysis (FIG. 6B).

Briefly, biotin-labeled DNA was synthesized and purchased from Allele Biotechlgy (Allele Biotechnology). Biotin-labeled RNA was synthesized with an AmpliScribe T7 transcription kit (Epicentre Technologies). The molar ratio of Biotin-UTP and (Clontech, Palo Alto, Calif.) and Biotin-CTP (Gibco) to natural UTP and CTP in the reaction was 1:5. Seventy microliters of streptavidin-conjugated agarose beads (Gibco BRL, Gaithersburg, Md.) were washed twice with binding buffer (20 mM Tris-HCl, pH 7.5, 60 mM KCl, 2.5 mM EDTA and 0.1% Triton X-100) and suspended in 100 µl of binding buffer. While the beads were kept on ice, 500 µL of cell extract from HCN A94 cells was mixed with 70 µg of biotinylated RNA. After incubation on ice for 10 min, the total volume was adjusted to 1 ml with binding buffer. Then the sample was transferred to the tube with agarose beads, and the tube was rotated slowly overnight at 4° C. The beads were washed 5 times with wash buffer (20 mM Tris-HCl, pH 7.5, 350 mM KCl and 0.01% NP-40) and resuspended in binding buffer. Proteins were eluted by boiling the beads and were separated by SDS-PAGE (7% polyacrylamide). For immunodetection of αNRSE/REST and αbeta-actin, proteins were transferred to a PVDF membrane and standard western blot analysis was performed.

The immunoblot revealed that both the NRSE dsDNA and the NRSE dsRNA bound NRSF/REST, demonstrating an association between NRSF/REST and the NRSE dsRNA.

To compare the affinity between NRSE dsDNA and NRSE dsRNA to NRSF/REST protein, an electrophoretic mobility shift assay (EMSA) was performed. NRSF/REST with cMyc-tag was expressed in 293T cells and immunoprecipitated with anti-cMyc antiboby. After purification, the protein was incubated with either NRSE dsDNAs or dsRNAs. A range of NRSF/REST protein concentrations was tested; the highest one tested produced a shift in dsDNA migration, whereas a 16-fold lower concentration of NRSF/REST protein was enough to produce a shift in dsRNA (FIG. 6C). Surprisingly, these data revealed that the affinity of NRSF/REST to the NRSE dsRNAs was much higher than the affinity to NRSE dsDNAs. Binding of NRSF/REST to the sequence of the MCS control dsRNAs or dsDNAs was not observed. Furthermore, no apparent band-shift was observed in samples of bovine serum albumin (BSA) incubated with NRSE dsRNAs or dsDNAs. This highly specific binding between NRSE dsRNA and NRSF/REST protein may contribute to a functional switch of the NRSF/REST machinery from transcriptional repressor to activator.

EXAMPLE XII

Expression of NRSF/REST Protein and NRSE dsRNA in the Adult Hippocampus

This example demonstrates the NRSE dsRNA is expressed in the adult hippocampus where it is highly restricted in the subgranular region of dentate gyrus, in a region where adult neurogenesis is continuously occurring.

Figure 7:
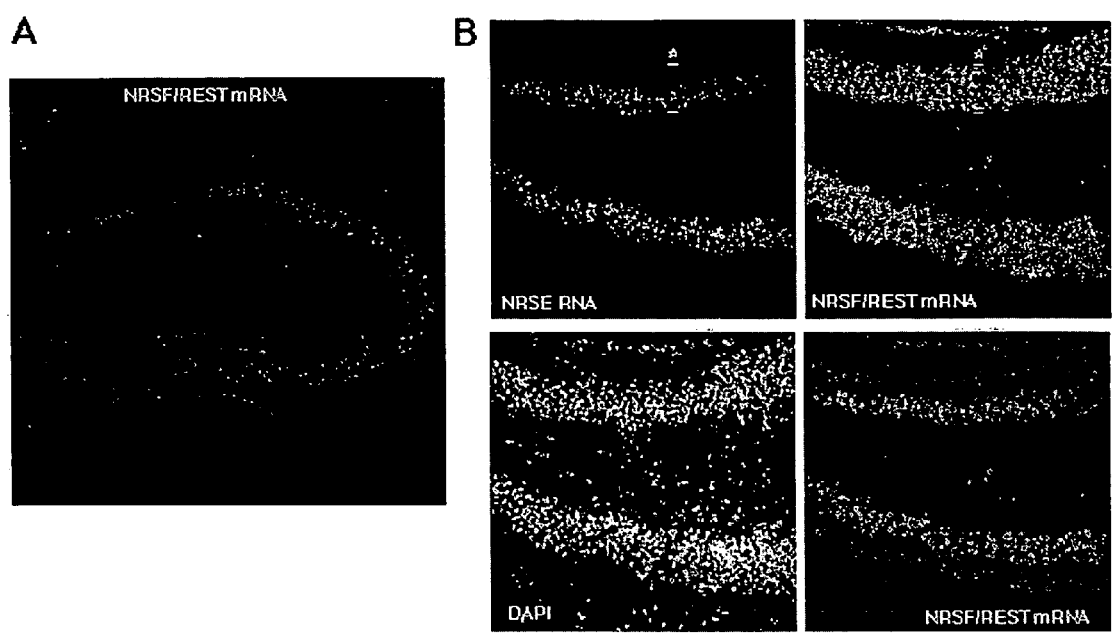
FIG. 7A shows in situ hybridization analysis for NRSF/REST mRNA and NRSE dsRNA in adult mouse hippocampus. NRSE dsRNA expression was highly restricted within the subgranular layer of the dentate gyrus, whereas NRSF/REST mRNA was expressed in a widespread neuronal area in adult hippocampus.
FIG. 7B shows a higher magnification view.

The expression of NRSF/REST mRNA and NRSE dsRNA in the adult mouse hippocampus was examined by in situ hybridization. Although NRSF/REST mRNA was expressed in non-neuronal glial cells (data not shown), the mRNA was highly expressed in hippocampal neurons (FIG. 7), suggesting that NRSF/REST is playing not only a role as a transcriptional repressor in non-neuronal cells but also a role in neurons in vivo. To verify the specificity of the in situ experiments, we did additional experiments with two negative control probes: a probe with the same nucleotide content containing a scrambled sequence and a probe with the same sequence in the reverse direction. There was no detectable signal with either negative control probe. An enlarged view of NRSF/REST and NRSE dsRNA expression is shown in FIG. 7B. Similar expression patterns of NRSF/REST have been previously documented (as described by Kallunki et al., *Proc. Natl. Acad. Sci. USA* 95:3233-3238 (1998); Palm et al., *J. Neurosci.* 18:1280-1296 (1998); Timmusk et al., *J. Biol. Chem.* 274:107-1084 (1999)). Interestingly, the expression of NRSE dsRNA was highly restricted in the subgranular region of dentate gyrus, in a region where adult neurogenesis is continuously occurring (as described by van Praag et al., *Nature* 415:1030-1034 (2002); Kempermann *Development* 130:391-399 (2003)) (FIG. 7), consistent with the in vitro data that NRSE dsRNAs function at an early stage in neuronal differentiation (FIGS. 1 and 2).

These results demonstrate the existence of interactions between proteins (NRSF/REST complex) and dsRNAs (the NRSE dsRNA) in addition to dsDNAs (NRSE/RE1 element). After the participation of dsRNAs in cells at early stages neurogenesis, the NRSF/REST complex alters binding partners from repressors to activators to initiate transcription of neuron specific genes. De-repression events can include global changes in cells, but at least the key players, proteins, dsDNAs and dsRNAs recognize each other within the nucleus in order to direct neurogenesis.

Throughout this application various publications have been referenced. The disclosures of these publications, each in its entirety, are hereby incorporated by reference in this application in order to more fully describe the state of the art to which this invention pertains. Although the invention has been described with reference to the examples provided above, it should be understood that various modifications can be made without departing from the spirit of the invention.

We claim:

1. A method for increasing transcription comprising:

contacting in vitro a cellular system comprising a regulatory machinery that controls transcription of one or more genes with a small modulatory double-stranded ribonucleic acid (smRNA) molecule, wherein:

(i) the regulatory machinery comprises a nucleic acid regulatory element located in a promoter region;

(ii) said one or more genes are specific to expression in the nervous system;

(iii) said nucleic acid regulatory element comprises a neuron-restrictive silencer element/repressor element 1 (NRSE/RE1); and (iv) the nucleic acid sequence of said smRNA molecule consists of SEQ ID NO:1 and a complementary sequence of SEQ ID NO:1.

2. The method of claim 1, wherein said regulatory machinery further comprises a trans-acting regulatory protein.

3. The method of claim 1, wherein said one or more genes have a pleiotropic effect.

4. The method of claim 1, wherein a vector is utilized to deliver said smRNA molecule to said cellular system.

5. The method of claim 4, wherein said vector is a viral vector.

6. The method of claim 5, wherein said viral vector is derived from a lentivirus.

7. The method of claim 1, wherein said one or more genes is selected from the group consisting of synapsin I, sodium channel type II, brain derived neurotrophic factor, Ng-CAM and L1.

8. The method of claim 1, wherein said one or more genes are involved in differentiation of neuronal stem cells into neurons.

9. A method for directing the differentiation of neuronal stem cells into neurons by increasing transcription of one or more genes involved in differentiation of neuronal stem cells, comprising contacting in vitro a neuronal stem cell comprising a regulatory machinery that controls transcription of one or more genes involved in neuronal differentiation with a small modulatory double-stranded ribonucleic acid (smRNA) molecule, wherein: (i) the regulatory machinery comprises a nucleic acid regulatory element located in a promoter region;

(ii) said one or more genes are specific to expression in the nervous system;

(iii) said nucleic acid regulatory element comprises a neuron-restrictive silencer element/repressor element 1 (NRSE/RE1); and (iv) the nucleic acid sequence of said smRNA molecule consists of SEQ ID NO: 1 and a complementary sequence of SEQ ID NO:1.

10. The method of claim 1, wherein the transcription is measured by a reporter assay.

11. The method of claim 1, wherein the transcription is measured by RT-PCR.

12. The method of claim 4, wherein the transcription is measured by a reporter assay.

13. The method of claim 4, wherein the transcription is measured by RT-PCR.

* * * * *

UNITED STATES PATENT AND TRADEMARK OFFICE
CERTIFICATE OF CORRECTION

| | | |
|---|---|---|
| PATENT NO. | : 8,092,992 B2 | Page 1 of 6 |
| APPLICATION NO. | : 10/857784 | |
| DATED | : January 10, 2012 | |
| INVENTOR(S) | : Kuwabara et al. | |

It is certified that error appears in the above-identified patent and that said Letters Patent is hereby corrected as shown below:

<u>Title Page, Item (56) Under Other Publications:</u>

Page 1, column 1, Jedruski et al., "histon H1 isoform (H1.1) is esential" should read --histone H1 isoform (H1.1) is essential--.

Page 1, column 1, Tuschl et al., "anaylsis" should read --analysis--.

Page 2, column 2, Roopra et al., "HIstone" should read --Histone--.

<u>Title Page, Item (57) In the Abstract:</u>

Column 2, line 6 of the Abstract, "directed to" should read --directed to a--.

<u>In the Specification:</u>

Column 2, line 3, "transcriptiponal" should read --transcriptional--.

Column 2, line 13, "the the" should read --the--.

Column 2, lines 25-28, "FIG. 1 shows identification of the NRSE dsRNA from adult hippocampal neuronal cells. FIG. 1A shows the sequence that contained a match to the 21-nt NRSE/RE1 DNA sequence in the antisense orientation shown in pink" should read --FIG. 1A schematically illustrates NRSE dsRNA from adult hippocampal neuronal cells. Sequences that contained a match to the 21-nt NRSE/RE1 DNA sequence (SEQ ID NOS: 3 and 4) are shown in the antisense orientation (SEQ ID NOS: 5-10, top to bottom)--.

Column 2, line 29, "FIG. 1B shows northern blotting analysis of the NRSE dsRNA" should read --FIG. 1B is an image showing a northern blotting analysis of NRSE dsRNA--.

Column 2, line 29, "FIG. 1C shows" should read --FIG. 1C is an image showing a--.

Column 2, line 38, "FIG. 2 shows" should read --FIG. 2A is an image showing--.

Signed and Sealed this
Twenty-first Day of May, 2013

Teresa Stanek Rea
*Acting Director of the United States Patent and Trademark Office*

Column 2, line 39, "In FIG. 2A, the NRSE" should read --The NRSE--.

Column 2, line 43, "FIG. 2B shows" should read --FIG. 2B is an image showing--.

Column 2, line 44, "FIG. 2C shows" should read --FIG. 2C is set of images and bar graphs showing--.

Column 2, line 50, "FIG. 3 shows" should read --FIGS. 3A-D show--.

Column 2, line 52, "FIG. 3A shows" should read --FIG. 3A is an image showing--.

Column 2, line 59, "(right) FIG. 3C shows a schematic diagram of the" should read --(right). FIG. 3C are schematic diagrams of the--.

Column 2, line 61, "of NRSE." should read --of NRSE. Sequences of the NRSE elements are shown below the schematic diagrams in the following order from top to bottom: SEQ ID NO: 4; SEQ ID NO: 13; SEQ ID NO: 14; SEQ ID NO: 15; SEQ ID NO: 16; SEQ ID NO: 17; SEQ ID NO: 18--.

Column 2, line 62, "FIG. 3D shows" should read --FIG. 3D is a series of bar graphs showing--.

Column 2, line 65, "FIG. 4 shows" should read --FIGS. 4A-C show--.

Column 2, line 66, "FIG. 4A shows" should read --FIG. 4A is an image showing--.

Column 3, line 1, "FIG. 4B shows" should read --FIG. 4B is an image showing--.

Column 3, line 4, "FIG. 4C shows a" should read --FIG. 4C is a schematic illustration showing--.

Column 3, line 8, "constructswere" should read --constructs were--.

Figure 5:
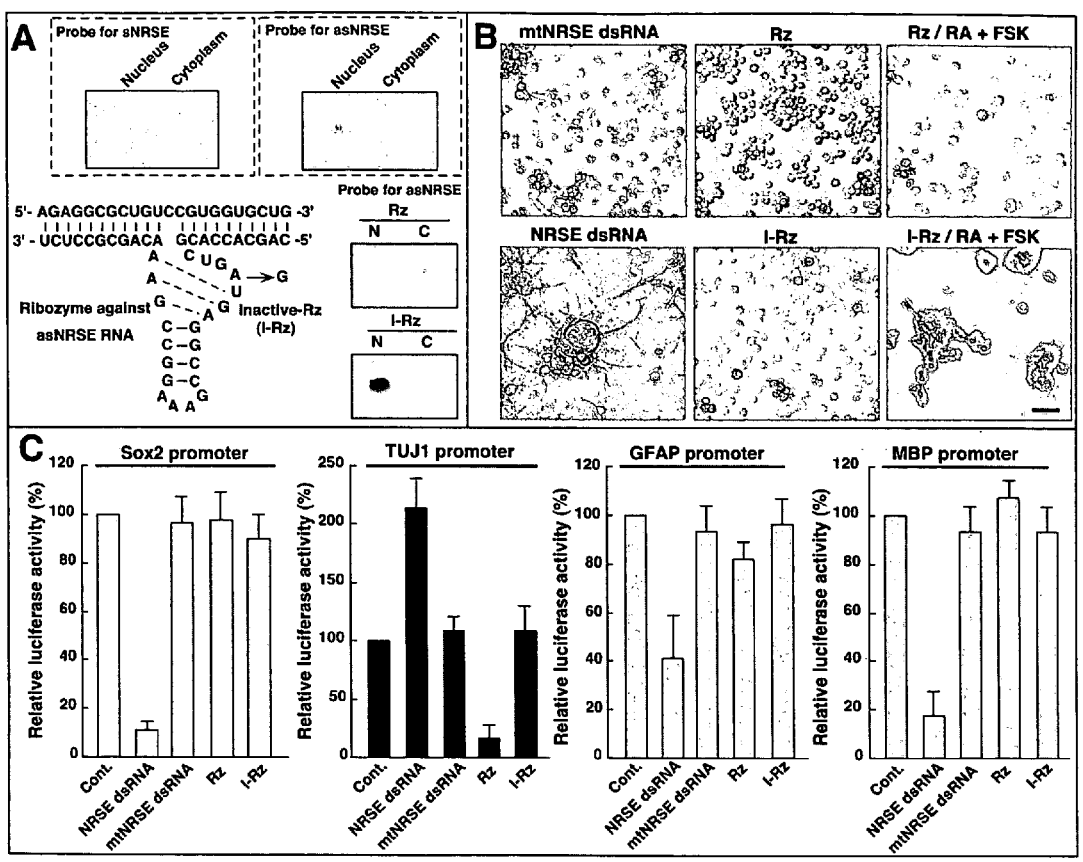
FIG. 5 shows that loss of NRSE dsRNA blocks neuronal differentiation.

Column 3, lines 11-15, "Figure 5 shows that loss of NRSE dsRNA blocks neuronal differentiation. Figure 5A shows the ribozyme (Rz) sequence designed to cleave the asNRSE RNA. Figure 5B shows-that cells with Rz cleaving NRSE RNAs showed strong anti-differentiation effects. Figure 5C shows the effect" should read --Figures 5A-B show that loss of NRSE dsRNA blocks neuronal differentiation. Figure 5A shows images and a schematic illustration of the ribozyme (Rz) sequence (SEQ ID NO: 16) designed to cleave the asNRSE RNA (the depicted target corresponds to nucleotides 1-22 of SEQ ID NO: 6). Figure 5B is a set of images of photomicrographs showing that cells with Rz cleaving NRSE RNAs showed strong anti-differentiation effects. Figure 5C is a series of bar graphs showing the effect--.

Figure 6:
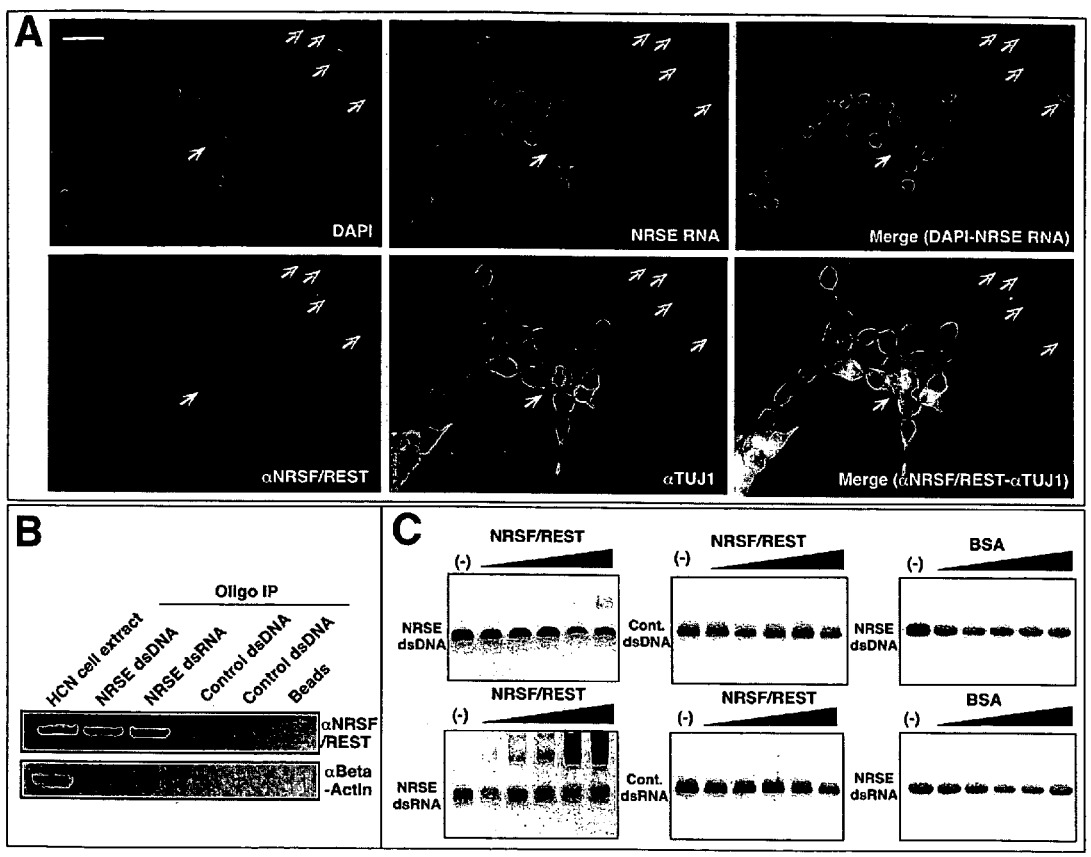
FIG. 6 shows the Localization of NRSE dsRNAs in the nucleus in neuronal cells and their interaction with NRSF/REST protein.

Column 3, lines 19-28, "Figure 6 shows the Localization of NRSE dsRNAs in the nucleus in neuronal cells and their interaction with NRSF/REST protein. Figure 6A shows-nuclear localization of the NRSE dsRNA in cells differentiating to neuron. Figure 6B shows-binding of the NRSE dsRNA to endogenous NRSF/REST protein. Figure 6C shows an results of an EMSA of NRSF/REST protein against NRSE dsRNA and dsDNA.

CERTIFICATE OF CORRECTION (continued)
U.S. Pat. No. 8,092,992 B2

While the concentration of each nucleotide was fixed as 20 µM, protein amount was increased 2-fold by each lane depending on arrow direction" should read --Figures 6A-C show the localization of NRSE dsRNAs in the nucleus in neuronal cells and their interaction with NRSF/REST protein. Figure 6A is a set of images of photomicrographs showing nuclear localization of the NRSE dsRNA in cells differentiating into neurons. Figure 6B is an image showing binding of the NRSE dsRNA to endogenous NRSF/REST protein. Figure 6C is a set of images showing results of an EMSA of NRSF/REST protein against NRSE dsRNA and dsDNA. While the concentration of each nucleotide was fixed as 20 µM, protein amount was increased 2-fold as indicated by the arrow direction--.

Column 3, line 29, "FIG. 7A shows" should read --FIGS. 7A and B are images showing--.

Column 3, line 31, "NRSE dsRNA" should read --FIG. 7A shows that NRSE dsRNA--.

Column 3, line 40, "binds to" should read --binding to--.

Column 3, lines 42-43, "FIG. 9 provides a table listing further genes that contain the NRSE motif and can be modulated via the invention methods" should read --FIGS. 9A and B provide a table listing additional genes that contain the NRSE motif and can be modulated via the disclosed methods--.

Column 4, line 58, "represnets" should read --represents--.

Column 4, line 59, "unique the" should read --unique to the--.

Column 5, line 1, "facors" should read --factor--.

Column 5, lines 21-22, "committment" should read --commitment--.

Column 5, line 26, "dsRNAs" should read --dsRNA--.

Column 6, line 8, "with the either" should read --with either--.

Column 7, line 29, "(1995b)" should read --(1995)--.

Column 7, line 31, "referwnce" should read --reference--.

Column 7, line 56, "referwnce" should read --reference--.

Column 7, line 61, "rexpression" should read --expression--.

Column 8, line 13, "molecule. The" should read --molecule (SEQ ID NO: 16). The--.

Column 8, lines 15-16. "5'-UUCAGCACCACGGACAGCGCC-3'" should read --5'-UUCAGCACCACGGACAGCGCC-3' (SEQ ID NO: 1)--.

Column 8, line 58, "can embedded at any location with in" should read --can be embedded at any location within--.

CERTIFICATE OF CORRECTION (continued)
U.S. Pat. No. 8,092,992 B2

Column 8, line 60, "6' UTR" should read --5' UTR--.

Column 9, line 3, "8 or more 9" should read --8 or more, 9--.

Column 9, line 12, "the both the" should read --both the--.

Column 9, line 14, "can further modified" should read --can further be modified--.

Column 9, line 66, "sequence," should read --sequence (SEQ ID NO: 2),--.

Column 10, lines 6-7, "UUCAGCACCACGGACAGCGCC-SPACER-AAGUCGUGGUGCCUGUCGCGG" should read --UUCAGCACCACGGACAGCGCC (SEQ ID NO: 1)-SPACER-AAGUCGUGGUGCCUGUCGCGG (SEQ ID NO: 2)--.

Column 10, line 22, "acid" should read --acids--.

Column 10, line 36, "disctinct" should read --distinct--.

Column 10, line 60, "of invention" should read --of the invention--.

Column 11, line 49, "in vivo; or" should read --in vivo, or--.

Column 14, line 37, "an in vitro" should read --in vitro--.

Column 14, lines 60-61, "ds RNA" should read --dsRNA--.

Column 15, lines 9-10, "genes NRSE-containing genes" should read --NRSE-containing genes--.

Column 15, line 48, "spefific" should read --specific--.

Column 15, line 59, "evidence" should read --evidenced--.

Column 15, line 51, "*Procl.*" should read --*Proc.*--.

Column 16, line 10, "deactylase" should read --deacetylase--.

Column 16, line 21, "transcritional" should read --transcriptional--.

Column 16, line 39-40, "FIG. 9 pro-vides" should read --FIGS. 9A and B provide--.

Column 17, line 10, "interferes a" should read --interferes with a--.

Column 17, line 11, "associats" should read --associates--.

Column 17, line 36, "molecule activity can" should read --molecule can--.

Column 17, line 59, "tis" should read --its--.

Column 18, line 2, "speficic" should read --specific--.

Column 18, line 41, "invovled" should read --involved--.

Column 18, line 46, "particlar" should read --particular--.

Column 18, line 61, "*Viol.*" should read --*Virol.*--.

Column 19, line 9, "WO 92/14829" should read --WO 92/14829)--.

Column 19, line 53, "transducted" should read --transduced--.

Column 19, line 61, "et., 1999" should read --ed., 1999--.

Column 20, line 9, "intergrate" should read --integrate--.

CERTIFICATE OF CORRECTION (continued)
U.S. Pat. No. 8,092,992 B2

Column 20, line 31, "an vector" should read --a vector--.

Column 20, line 46, "can ne used to target the dsRNA to te dsired" should read --can be used to target the dsRNA to the desired--.

Column 21, line 52, "manfacture's" should read --manufacturer's--.

Column 22, line 52, "induce" should read --induces--.

Column 22, line 60, "descibed" should read --described--.

Column 23, line 2, "U6 driven each NRSE" should read --Each U6 driven NRSE--.

Column 23, line 9, "was constructed" should read --were constructed--.

Column 23, line 11, "sequeunce" should read --sequence--.

Column 23, line 21, "□III" should read --βIII--.

Column 23, line 52, "reduced the" should read --reduced when the--.

Column 23, line 60, "permeablization" should read --permeabilization--.

Column 24, line 23, "□III" should read --βIII--.

Column 24, line 49, "values" should read --value--.

Column 25, lines 4-5, "culture (data not shown)" should read --culture--.

Column 25, line 56, "mRNA/siRNA-like" should read --miRNA/siRNA-like--.

Column 26, line 20, "mRNA/siRNAs" should read --miRNA/siRNA--.

Column 26, line 50, "mRNA/siRNA-like" should read --miRNA/siRNA-like--.

Column 27, line 63, "(1995b)'" should read --(1995)--.

Column 27, line 65, "stern" should read --stem--.

Column 28, line 56, "RNAs" should read --RNA--.

Column 29, line 18, "Trancriptional" should read --Transcriptional--.

Column 30, line 6, "tools" should read --tool--.

Column 30, line 30, "dsRN" should read --dsRNA--

Column 31, line 39, "magenta, FIG. 6A" should read --FIG. 6A--.

Column 31, line 41, "□III" should read --βIII--.

Column 31, line 42, "(Yellow) positive" should read --positive--.

Column 31, line 42, "(Red arrows" should read --(Center arrow--.

Column 31, line 45, "(Blue" should read --(Upper right-- .

Column 31, line 48, "dsRNAs" should read --dsRNA--.

Column 31, line 49, "positive" should read --positive)--.

Column 32, line 4, "Biotechlogy" should read --Biotechnology--.

Column 32, line 7, "and (Clontech" should read --(Clontech--.

Column 32, line 33, "antiboby" should read --antibody--.

CERTIFICATE OF CORRECTION (continued)
U.S. Pat. No. 8,092,992 B2

Column 32, line 62, "cells (data not shown), the" should read --cells, the--.

Column 32, line 67, "we did additional experiments with two" should read --additional experiments were performed with two--.

Column 33, line 10, "107-1084" should read --1078-1084--.

Column 34, line 4, "stages" should read --stages of--.

SEQUENCE LISTING

```
<160> NUMBER OF SEQ ID NOS: 16

<210> SEQ ID NO 1
<211> LENGTH: 21
<212> TYPE: RNA
<213> ORGANISM: Homo sapiens

<400> SEQUENCE: 1
uucagcacca cggacagcgc c                                              21

<210> SEQ ID NO 2
<211> LENGTH: 21
<212> TYPE: RNA
<213> ORGANISM: Artificial Sequence
<220> FEATURE:
<223> OTHER INFORMATION: Reverse complement of SEQ ID NO: 1

<400> SEQUENCE: 2
aagucguggu gccugucgcg g                                              21

<210> SEQ ID NO 3
<211> LENGTH: 21
<212> TYPE: DNA
<213> ORGANISM: Artificial Sequence
<220> FEATURE:
<223> OTHER INFORMATION: NRSE/REl

<400> SEQUENCE: 3
ttcagcacca cggacagcgc c                                              21

<210> SEQ ID NO 4
<211> LENGTH: 21
<212> TYPE: DNA
<213> ORGANISM: Artificial Sequence
<220> FEATURE:
<223> OTHER INFORMATION: NRSE/REl

<400> SEQUENCE: 4
ggcgctgtcc gtggtgctga a                                              21

<210> SEQ ID NO 5
<211> LENGTH: 24
<212> TYPE: RNA
<213> ORGANISM: Artificial Sequence
<220> FEATURE:
<223> OTHER INFORMATION: asNRSE
```

-continued

<400> SEQUENCE: 5
aaggcgcugu ccguggugcu gaau                                                24

<210> SEQ ID NO 6
<211> LENGTH: 26
<212> TYPE: RNA
<213> ORGANISM: Artificial Sequence
<220> FEATURE:
<223> OTHER INFORMATION: asNRSE

<400> SEQUENCE: 6
agaggcgcug uccguggugc ugaauu                                              26

<210> SEQ ID NO 7
<211> LENGTH: 24
<212> TYPE: RNA
<213> ORGANISM: Artificial Sequence
<220> FEATURE:
<223> OTHER INFORMATION: asNRSE

<400> SEQUENCE: 7
gaggcgcugu ccguggugcu gaau                                                24

<210> SEQ ID NO 8
<211> LENGTH: 25
<212> TYPE: RNA
<213> ORGANISM: Artificial Sequence
<220> FEATURE:
<223> OTHER INFORMATION: asNRSE

<400> SEQUENCE: 8
cuaggcgcug uccguggugc ugaau                                               25

<210> SEQ ID NO 9
<211> LENGTH: 22
<212> TYPE: RNA
<213> ORGANISM: Artificial Sequence
<220> FEATURE:
<223> OTHER INFORMATION: asNRSE

<400> SEQUENCE: 9
ggcgcugucc guggugcuga au                                                  22

<210> SEQ ID NO 10
<211> LENGTH: 23
<212> TYPE: RNA
<213> ORGANISM: Artificial Sequence
<220> FEATURE:
<223> OTHER INFORMATION: asNRSE

<400> SEQUENCE: 10
gaggcgcugu ccguggugcu gaa                                                 23

<210> SEQ ID NO 11
<211> LENGTH: 21
<212> TYPE: DNA
<213> ORGANISM: Artificial Sequence
<220> FEATURE:
<223> OTHER INFORMATION: mutant NRSE/RE1

<400> SEQUENCE: 11
ttcagcacca caaacagcgc c                                                   21

<210> SEQ ID NO 12
<211> LENGTH: 21

```
<212> TYPE: DNA
<213> ORGANISM: Artificial Sequence
<220> FEATURE:
<223> OTHER INFORMATION: mutant NRSE/REI
<220> FEATURE:
<221> NAME/KEY: misc_feature
<222> LOCATION: (9)..(10)
<223> OTHER INFORMATION: n = u

<400> SEQUENCE: 12
ggcgctgtnn gtggtgctga a                                              21

<210> SEQ ID NO 13
<211> LENGTH: 21
<212> TYPE: RNA
<213> ORGANISM: Artificial Sequence
<220> FEATURE:
<223> OTHER INFORMATION: NRSE/REI ds RNA

<400> SEQUENCE: 13
ggcgcugucc guggugcuga a                                              21

<210> SEQ ID NO 14
<211> LENGTH: 21
<212> TYPE: RNA
<213> ORGANISM: Artificial Sequence
<220> FEATURE:
<223> OTHER INFORMATION: NRSE/REI ds RNA

<400> SEQUENCE: 14
uucauuacca cccacagcgc c                                              21

<210> SEQ ID NO 15
<211> LENGTH: 21
<212> TYPE: RNA
<213> ORGANISM: Artificial Sequence
<220> FEATURE:
<223> OTHER INFORMATION: NRSE/REI ds RNA

<400> SEQUENCE: 15
ggcgcugugg gugguaauga a                                              21

<210> SEQ ID NO 16
<211> LENGTH: 43
<212> TYPE: RNA
<213> ORGANISM: Artificial Sequence
<220> FEATURE:
<223> OTHER INFORMATION: Ribozyme

<400> SEQUENCE: 16
cagcaccacg cugaugaggc cgaaaggccg aaacagcgcc ucu                      43
```